US009446051B2

(12) United States Patent
Sitruk-Ware et al.

(10) Patent No.: US 9,446,051 B2
(45) Date of Patent: Sep. 20, 2016

(54) NEUROPROTECTION AND MYELIN REPAIR USING NESTORONE®

(71) Applicant: The Population Council, Inc., New York, NY (US)

(72) Inventors: Regine Sitruk-Ware, New York, NY (US); Michael Maria Helmut Schumacher, Kremlin-Bicêtre (FR); Roberta Brinton, Rancho Palos Verdes, CA (US); Martine El-Etr, Paris (FR); Abdelmouman Ghoumari, Antony (FR); Rachida Guennoun, Villejuif (FR)

(73) Assignee: The Population Council, Inc., New York, NY (US)

( * ) Notice: Subject to any disclaimer, the term of this patent is extended or adjusted under 35 U.S.C. 154(b) by 470 days.

(21) Appl. No.: 13/725,064

(22) Filed: Dec. 21, 2012

(65) Prior Publication Data

US 2013/0116217 A1   May 9, 2013

Related U.S. Application Data

(63) Continuation-in-part of application No. 13/500,008, filed as application No. PCT/US2010/053201 on Oct. 19, 2010.

(60) Provisional application No. 61/279,320, filed on Oct. 19, 2009.

(51) Int. Cl.
| | |
|---|---|
| *A61K 31/57* | (2006.01) |
| *A61K 31/575* | (2006.01) |
| *A61K 31/58* | (2006.01) |
| *A61K 31/567* | (2006.01) |
| *A61K 31/565* | (2006.01) |
| *A61K 31/569* | (2006.01) |

(52) U.S. Cl.
CPC ............ *A61K 31/567* (2013.01); *A61K 31/565* (2013.01); *A61K 31/569* (2013.01); *A61K 31/57* (2013.01); *A61K 31/575* (2013.01); *A61K 31/58* (2013.01)

(58) Field of Classification Search
CPC .......................... A61K 31/57; A61K 31/565
USPC ........................................................ 514/180
See application file for complete search history.

(56) References Cited

U.S. PATENT DOCUMENTS

| | | | | |
|---|---|---|---|---|
| 4,760,092 | A | | 7/1988 | Weinreb |
| 6,891,081 | B1 | * | 5/2005 | Stern .................. A01K 67/0275 435/320.1 |
| 8,026,228 | B2 | * | 9/2011 | Coelingh Bennink A61K 31/56 514/10.2 |
| 2002/0049495 | A1 | * | 4/2002 | Kutryk et al. ................ 623/1.47 |

| | | | |
|---|---|---|---|
| 2004/0087563 | A1 | 5/2004 | Mayerhofer |
| 2005/0014731 | A1 | 1/2005 | Alt et al. |
| 2006/0205704 | A1 | 9/2006 | Scott et al. |

FOREIGN PATENT DOCUMENTS

| | | |
|---|---|---|
| CN | 102657661 A | 9/2012 |
| CN | 102688247 A | 9/2012 |
| WO | 03097071 A1 | 11/2003 |
| WO | 2008150547 A1 | 12/2008 |
| WO | 2011049948 A2 | 4/2011 |

OTHER PUBLICATIONS

Australian Examination Report for Application No. 2010308308 dated Aug. 23, 2013.
Lenzi E et al: "Central modifications of allopregnanolone and beta-endorphin following subcutaneous administration of Nestorone", Journal of Steroid Biochemistry and Molecular Biology, Elsevier Science Ltd., Oxford, GB, vol. 116, No. 1-2, Aug. 1, 2009, pp. 15-20, XP026211788.
Schumacher et al: "Progesterone and progestins: neuroprotection and myelin repair", Current Opinion in Pharmacology , Elsevier Science Publishers, NL, vol. 8, No. 6, Dec. 1, 2008, pp. 740-746, XP025669940.
Birgbauer et al., "Lysolecithin induces demyelination in Vitro in a cerebellar slice culture system", Journal of Neuroscience Research 78:157-166 (2004).
Brinton et al., "Progesterone Receptors: Form and Function in Brain", Front Neuroendocrinol. May 2008; 29(2): 313-339.
Communication from PCT/US2010/053201, dated Jan. 19, 2011.
Confavreux et al., "Natural history of multiple sclerosis a unifying concept", Brain (2006), 129, 606-616.
Confavreux et al., "Rate of pregnancy-related relapse in multiple sclerosis", The New England Journal of Medicine, vol. 339, No. 5, Jul. 30, 1998.
Confavreux et al., :Course and Prognosis of Multiple Sclerosis Assessed by the Computerized Data Processing of 349 Patients, Brain (1980), 103, pp. 281-300.
Dutta et al., "Pathogenesis of axonal and neuronal damage in multiple sclerosis", Neurology 2007; 68; S22-S31.
Ghoumari et al., "Progesterone and its metabolites increase myelin basic protein expression in organotypic slice cultures of rat cerebellum", Journal of Neurochemistry, 2003, 86, 848-859.

(Continued)

Primary Examiner — Jennifer M Kim
(74) Attorney, Agent, or Firm — Lerner, David, Littenberg, Krumholz & Mentlik, LLP

(57) ABSTRACT

Methods for treating neurodegeneration and/or myelination in patients are disclosed comprising treating the patient with a progestin compound which exerts binding to progesterone receptors and elicits progesterone-receptor-induced biological responses without interacting with the androgen receptor and without inducing androgen or glucocorticoid biological responses at a dosage sufficient to prevent or reduce neurodegeneration. The progestin compound preferably comprises 16-methylene-17α-acetoxy-19-norpregn-4-ene-3,20-dione, and the methods include combining the progestin compound with an estrogen compound to provide both contraception and treatment for myelin repair and neurodegeneration, and include effects on stroke and TBI.

10 Claims, 24 Drawing Sheets

(56) References Cited

OTHER PUBLICATIONS

Ghoumari et al., "Progesterone increases oligodendroglial cell proliferation in rat cerebellar slice cultures", Neuroscience 135 (2005) 47-58.

Gibson et al., "Progesterone for the treatment of experimental brain injury; a systematic review", Brain (2008), 131, 318-328.

Holmqvist et al., "Symptoms of multiple sclerosis in women in relation to sex steroid exposure", Maturitas 54 (2006) 149-153.

International Search Report and Written Opinion, PCT/US2010/053201, dated Apr. 19, 2011.

Irvine et al., "Remyelination protects axons from demyelination-associated axon degeneration", Brain (2008), 131, 1464-1477.

Kornek et al., "Multiple sclerosis and chronic autoimmune encephalomyelitis / A comparative quantitative study of axonal injury in active, inactive, and remyelinated lesions", American Journal of Pathology, vol. 157, No. 1, Jul. 2000.

Kumar et al., "Nestorone: a progestin with a unique pharmacological profile", Steroids 65 (2000) 629-636.

Liu et al., "Progesterone increases rat neural progenitor cell cycle gene expression and proliferation via exracellularly regulated kinase and progesterone receptor membrane components 1 and 2", Neuroendocrinology, Juy 2009, 15 (7):3186-3196.

Ming Wang et al., "Regenerative potential of alloprgnanolone", Brain Reserach Reviews, 57 (2008), pp. 398-409.

Nilsen et al., "Impact of progestins on estrogen-induced neuroprotection: Synergy by progesterone and 19- norprogesterone and antagonism by medroxyprogesterone acetate", Endocrinology 143(1): p. 205-212, Jan. 2002.

Patani et al., "Remyelination can be extensive in multiple sclerosis despite a long disease course", Neuropathalogy and Applied Neurobiology (2007), 33, 277-287.

Patrikios et al., "Remyelination is extensive in a subset of multiple sclerosis patients", Brain (2006), 129, 3165-3172.

Pugliatti et al., "The epidemiology of multiple sclerosis in Europe", Europena Journal of Neurology 2006, 13: 700-722.

Sayeed et al., "Progesterone inhibits ischemic brain injury in a rat model of permanent middle cerebral artery occlusion", Restorative Neurology and Neuroscience 25 (2007) 151-159.

Sitruk-Ware, Regine, "New progestagens for contraceptive use", Human Reproduction Update, vol. 12, No. 2, pp. 169-178, 2006.

Extended European Seach Report for Application No. EP13199399 dated Mar. 19, 2014.

Hussain Rashad et al: "Progesterone and Nestorone Facilitate Axon Remyelination: A Role for Progesterone Receptors", Endocrinology, vol. 152, No. 10, Oct. 2011, pp. 3820-3831, XP055106124.

Liu Ailing et al: "Progesterone Receptors: A Key for Neuroprotection in Experimental Stroke", Endocrinology, vol. 153, No. 8, Aug. 2012, pp. 3747-3757, XP055106120.

Stein et al: "Progesterone exerts neuroprotective effects after brain injury", Brain Research Reviews, Elsevier, NL, vol. 57, No. 2, Mar. 14, 2008, pp. 386-397, XP022540464.

European Examination Report for Application No. 10768168.6 dated Apr. 18, 2013.

Liu et al, "Clinically Relevant Progestins Regulate Neurogenic and Neuroprotective Responses in Vitro and in Vivo", Endocrinology, vol. 151 , No. 12, Dec. 1, 2010, pp. 5782-5794, xP008131261.

\* cited by examiner

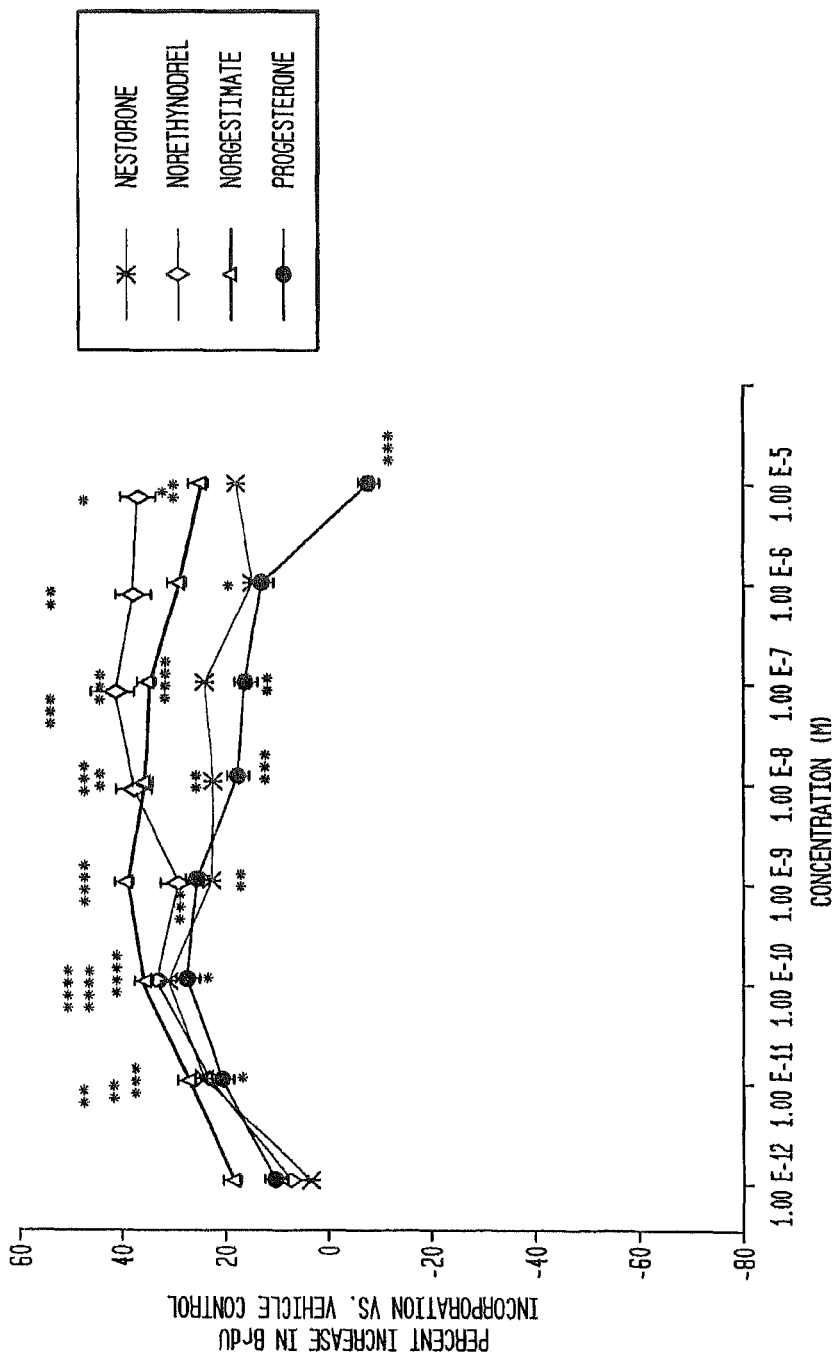

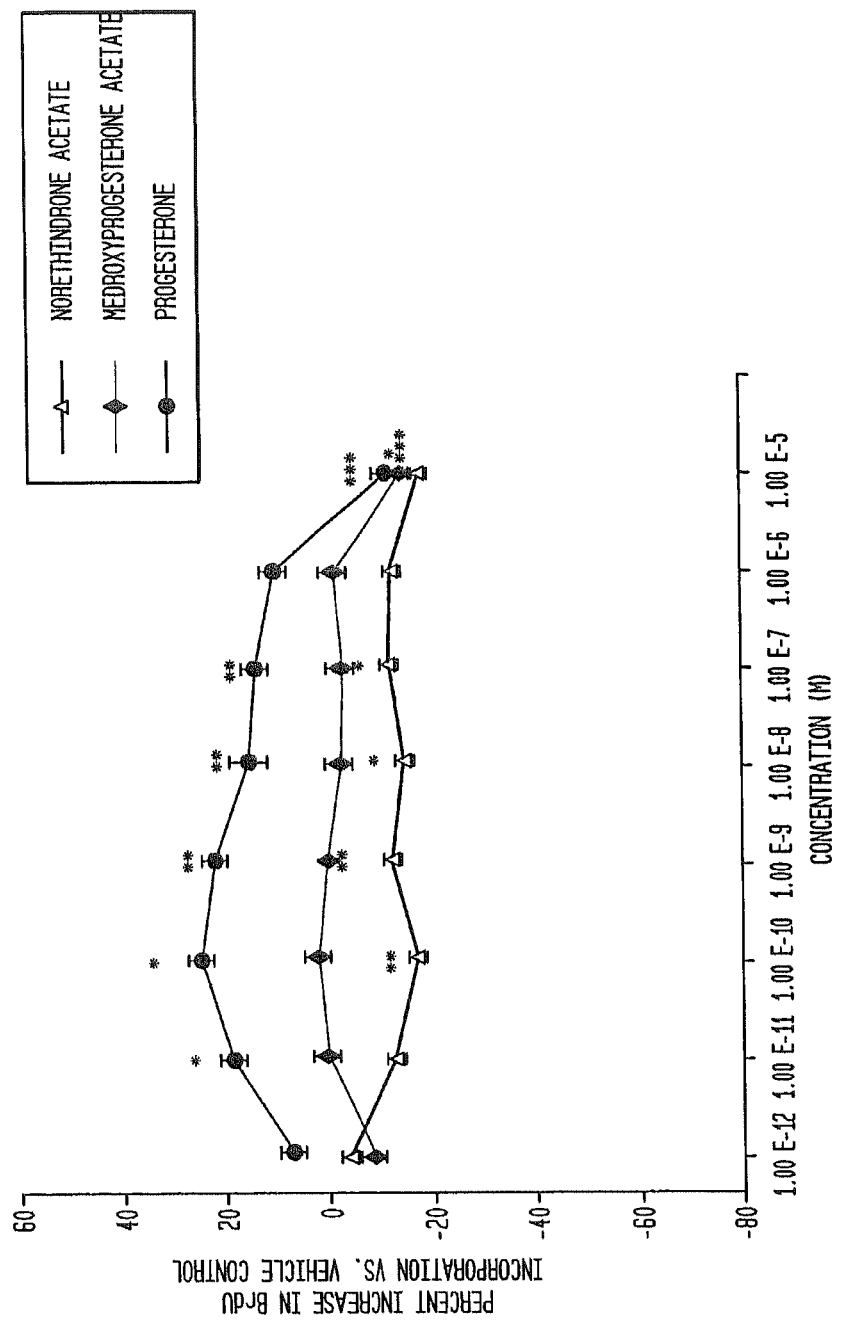

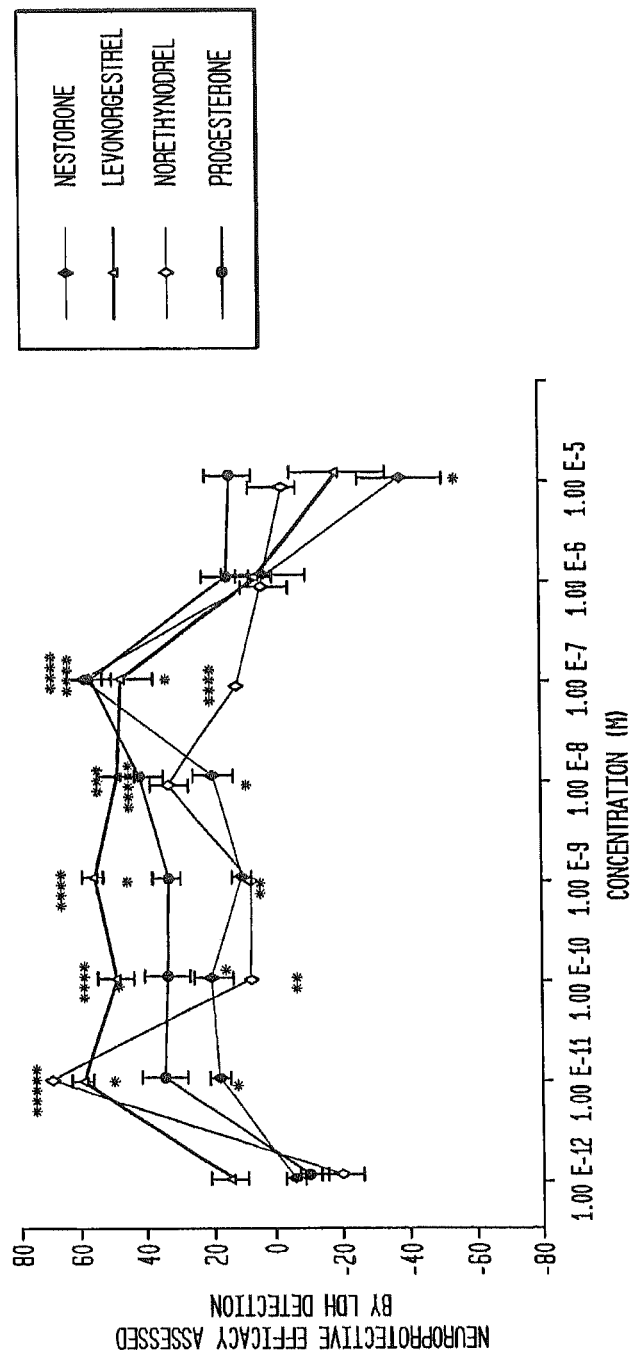

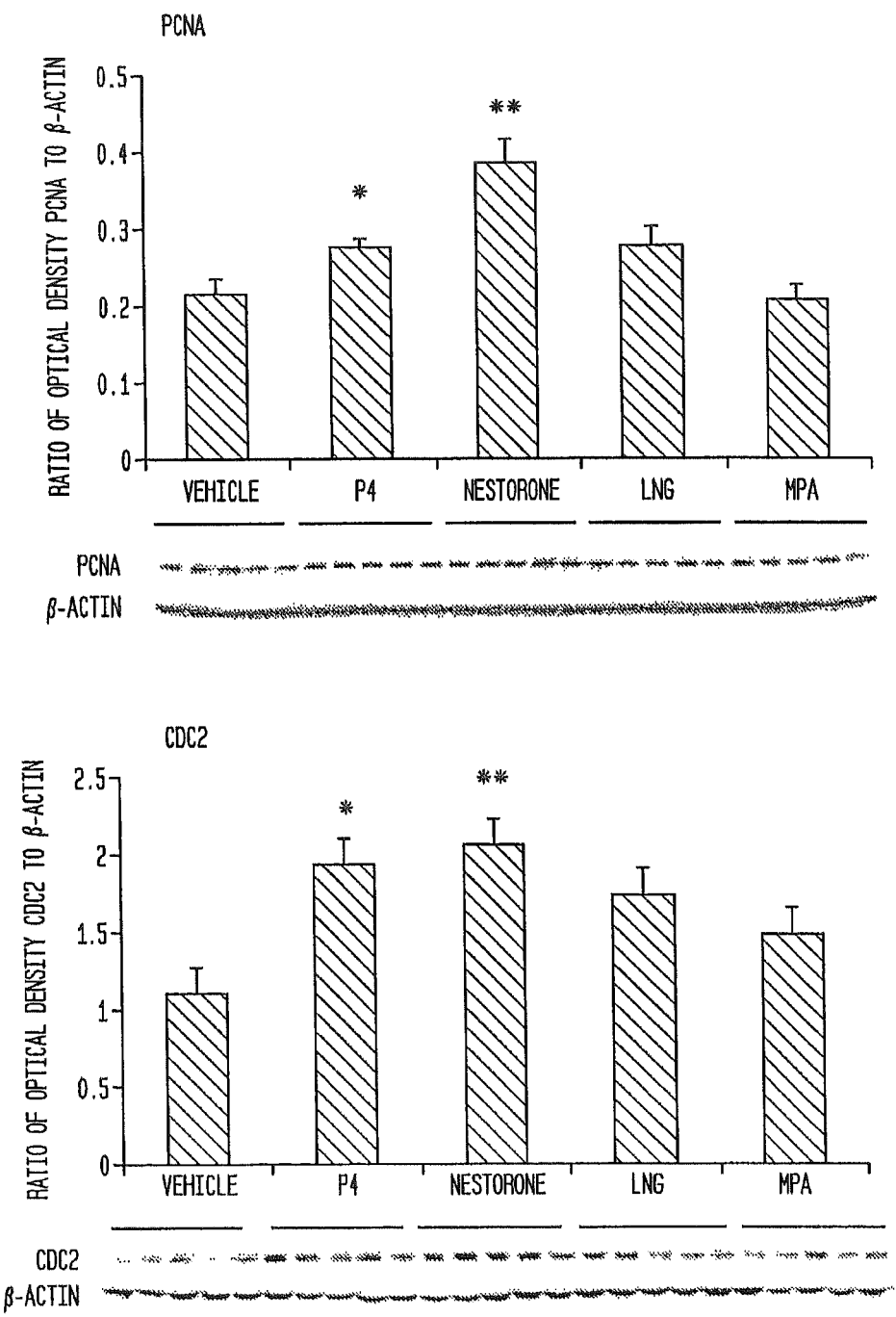

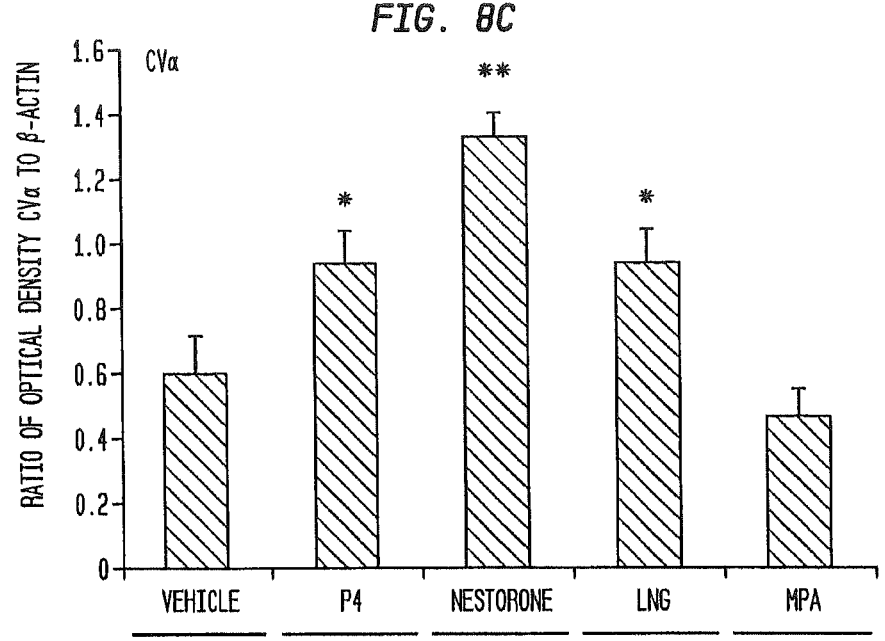
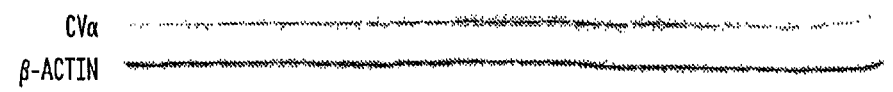
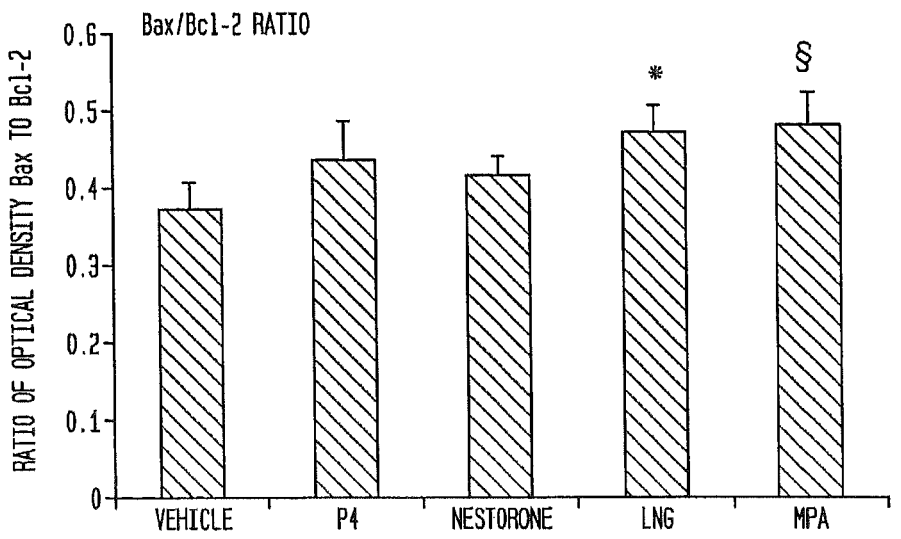
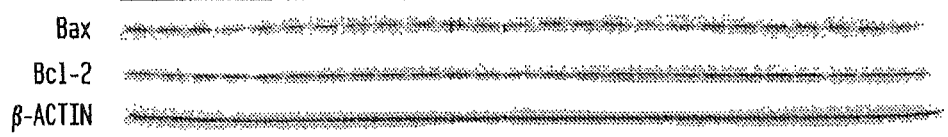
FIG. 8C

FIG. 10
NEURONAL DENSITY IN THE INFARCT, PENNUMBRA AND CONTRALATERAL HEMISPHERE 48H AFTER MCAO
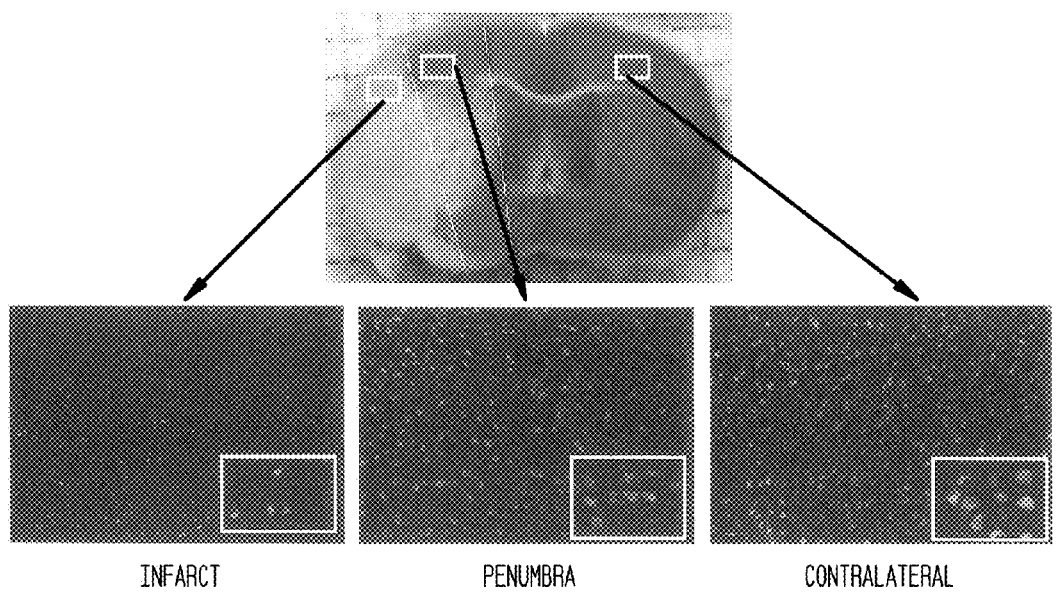
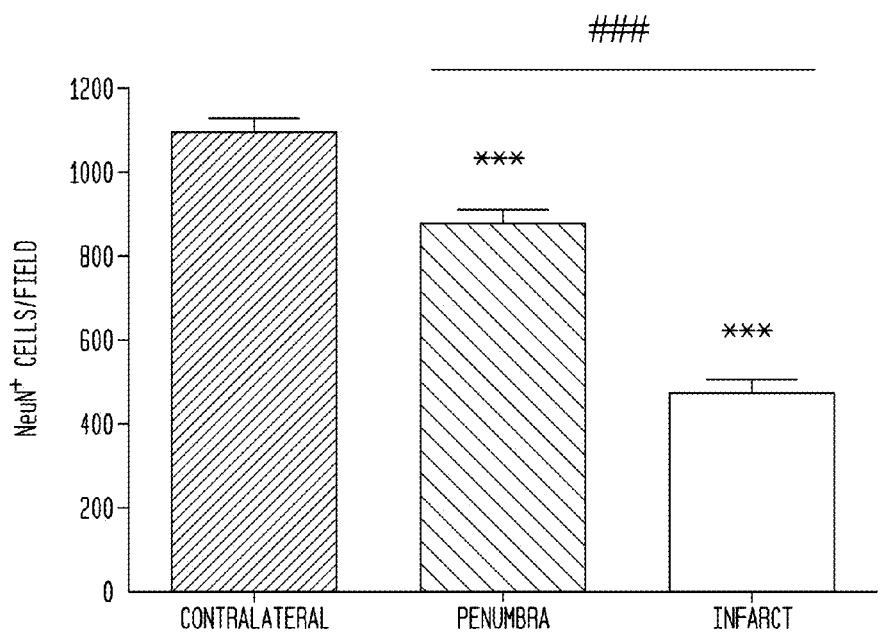

SYSTEMIC ADMINISTRATION OF PROGESTERONE INCREASED NEURONAL DENSITY IN THE INFARCT

FIG. 13
SYSTEMIC ADMINISTRATION OF PROGESTERONE DECREASED MICROGLIAL DENSITY IN THE PENUMBRA
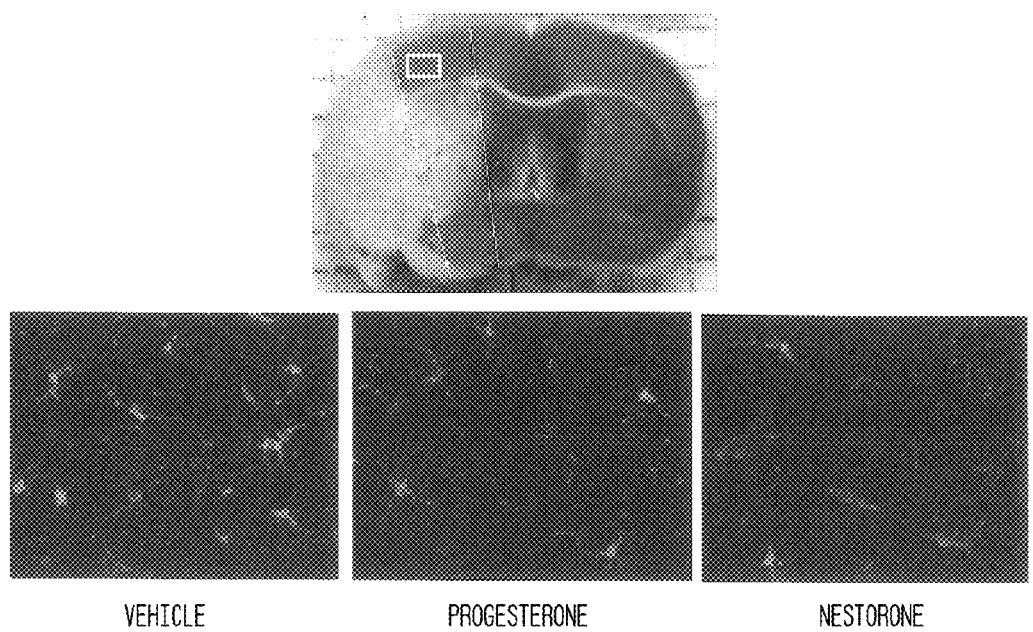
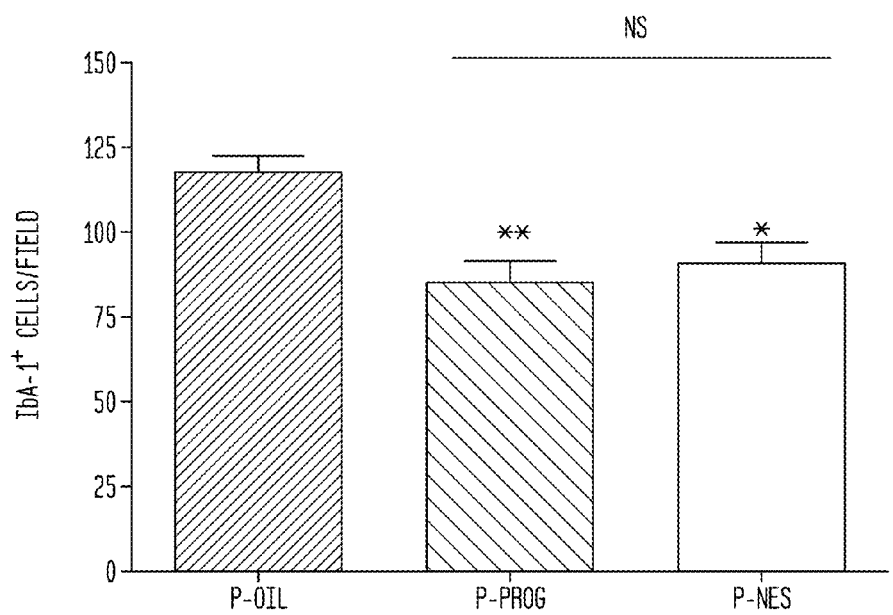

Liu et al. Endocrinology, in press.

FIG. 15
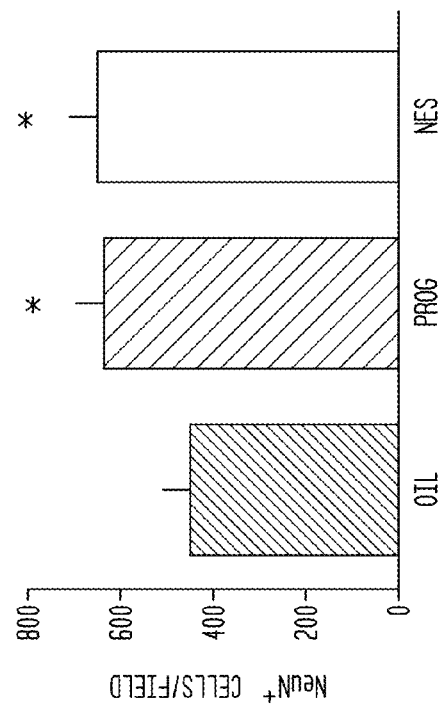
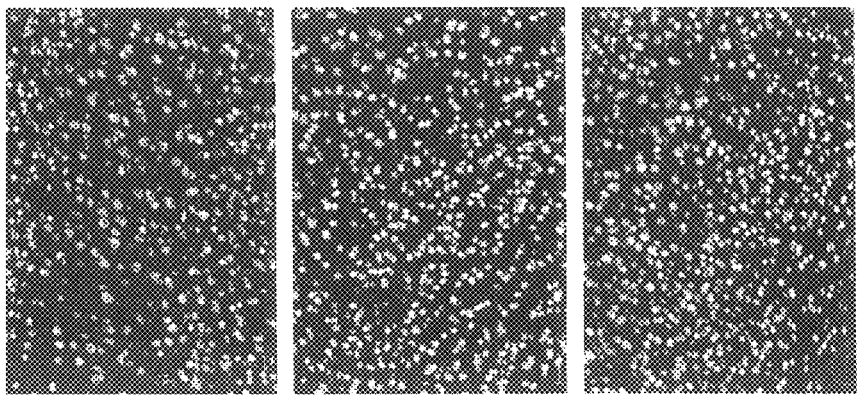

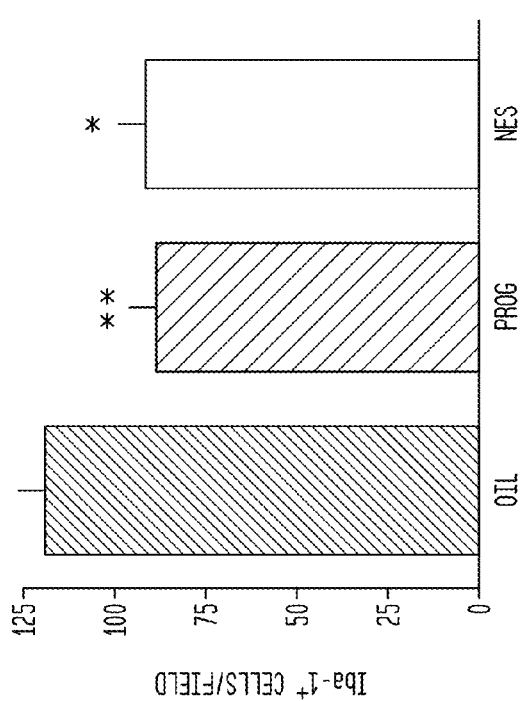
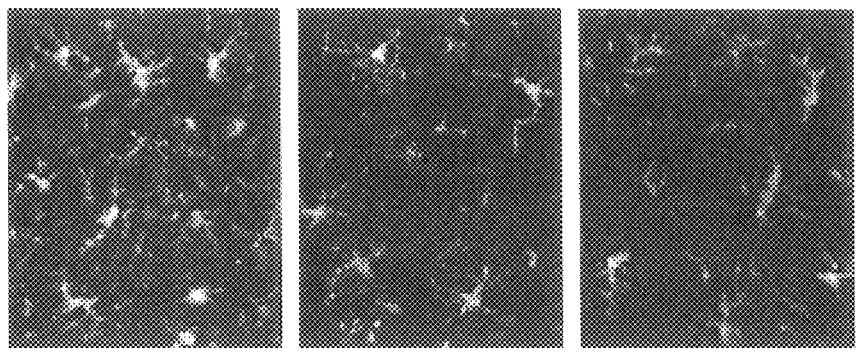
FIG. 18 SYSTEMIC ADMINISTRATION OF PROGESTERONE OR NESTORONE® DECREASED MICROGLIA IN THE PENUMBRA 48H AFTER MCAO

NEUROPROTECTION AND MYELIN REPAIR USING NESTORONE®

CROSS-REFERENCE TO RELATED APPLICATIONS

The present application is a continuation-in-part of application Ser. No. 13/500,008 filed on May 31, 2012, which is a national phase entry under 35 U.S.C. §371 of International Application No. PCT/US2010/53201 filed on Oct. 19, 2010, published in English, which claims the benefit of the filing date of U.S. Provisional Patent Application No. 61/279,320 filed Oct. 19, 2009, the disclosures of which are hereby incorporated herein by reference.

FIELD OF THE INVENTION

The present invention relates to the field of prevention of myelin degeneration and neurodegeneration. More particularly, the present invention relates to the prevention or treatment of degenerative aspects of diseases such as Multiple Sclerosis (MS), Alzheimer's Disease (AD) and Parkinson's Disease (PD), as well as for stroke. Even more particularly, the present invention relates to the prevention or treatment of ischemic damage such as from strokes or traumatic brain injury.

BACKGROUND OF THE INVENTION

Multiple Sclerosis (MS) is a progressive and disabling disease of the central nervous system (CNS) affecting more than twice as many women as men (1-4). Evidence suggests that neuronal damage begins early in MS (5), with acute axonal injury already present during active demyelination. However, remyelination is known to occur in MS (6,7) where it protects against axon loss (8). Indeed, no significant axonal damage can be observed in remyelinated plaques (5). Axons become less receptive to remyelination as MS progresses. Furthermore, a stroke is a cerebrovascular incident which also leads to neuronal damage. In an experimental model of transient middle cerebral artery occlusion (MCAO) the infarct volume induced by the occlusion was much larger in mice deprived of progesterone receptor (PR knockout mice) than in control intact mice.

The neurodegenerative process of several CNS diseases, including Multiple Sclerosis (MS), Alzheimer's Disease (AD) and Parkinson's Diseases (PD) involve neuroinflamation as well as neurodegeneration, and their frequency increases in women after menopause. Similar neurodegenerative processes are also present in patients suffering from ischemic damage, such as stroke patients, or those who have suffered the effects of a cerebrovascular incident, such as a traumatic brain injury (TBI).

Neuronal damage can also occur in other contexts, such as with a stroke. A stroke is a cerebral vascular incident which results from an interruption in the blood supply to brain cells. Neurons thus can be destroyed because of their sensitivity to oxygen and glucose deprivation, as well as from progressive spreading of nervous tissue damage from an infarct site. There have thus been serious efforts to treat stroke patients to both protect neurons from being destroyed and avoid the spreading of lesions as well as to support regeneration of damaged tissue. Progesterone has previously been identified as an efficient neuroprotective agent. Indeed, progesterone itself is produced at increased rate in brain cells after lesion occurs. Progesterone treatment has also been found to be effective in reducing lesion size following cerebral ischemia in animal models of stroke (18) and has been found to inhibit ischemic brain injury after brain artery occlusion (19). Stroke presents a major public health issue accounting for about over 100,000 cases annually. The only approved treatment for acute stroke is thrombolysis with tissue plasminogen activator (TPA) which has a limited therapeutic window and creates a risk of hemorrhaging.

Progestins such as Nestorone® have been found to exert proliferative and neuroprotective effects in the brain (20,21).

Approximately two-thirds of patients with relapsing-remitting MS are women of reproductive age. (9) It is known that a high level of female sex steroids, such as that which occurs during pregnancy, may be responsible for the remission of symptoms in women with MS. This is especially true during the third trimester when estrogen and progesterone (PROG) levels peak, while the relapse rate increases in the post-partum period. (9)

Women with MS experience changes in their MS symptoms related to pregnancy, the postpartum period, or menopause. In a study conducted in Sweden (10): 40% of the 148 women with MS who were interviewed reported worsening of MS symptoms related to menopause, and more than a fourth of the younger women reported decreased symptoms during pregnancy. Every third woman reported increased symptoms after delivery, suggesting that the sex steroids play a role in the protection (when present in high levels during pregnancy) or worsening of the disease (when they decrease after delivery or at menopause).

An effective treatment strategy for conditions such as MS must also include therapeutic agents that reverse axon demyelination in order to prevent irreversible axon loss. Estrogen and progesterone, female sex hormones, may have beneficial effects on MS and neuroprotection.

In primary hippocampal neuron cultures treated with 17β-E2 and progestins, alone and in combination, 48 hours before glutamate insult, estradiol, progesterone, and 19-norprogesterone, alone or in combination, protected against glutamate toxicity. In contrast, medroxyprogesterone acetate (MPA) failed to protect against glutamate toxicity. Not only was MPA an ineffective neuroprotectant, but it attenuated the estrogen-induced neuroprotection when coadministered (11). These results may have important implications for the maintenance of neuronal function during menopause and aging and for protection against neurodegenerative diseases such as Alzheimer's disease by selecting the appropriate molecules for hormone therapy Progesterone receptor (PR) expression and regulation of neural progenitor cell proliferation was investigated using NPC derived from adult rat brain. Progesterone mediated neural progenitor cell (NPC) proliferation and concomitant regulation of mitotic cell cycle genes is a potential novel therapeutic target for promoting neurogenesis in the mammalian brain (12).

SUMMARY OF THE INVENTION

In accordance with the present invention, these and other objects have now been realized by the discovery of a method for treating neurodegeneration in a patient comprising treating the patient with a pharmaceutically effective dosage of a progestin compound which exerts binding to progesterone receptors and elicits progesterone-receptor-induced biological responses without interacting with the androgen receptor and without inducing androgen or glucocorticoid biological responses. In the case of oral dosage forms, such as tablets, capsules, and the like, the pharmaceutically accepted dosage will be 5 mg/day or less, whereby neurodegeneration is prevented or reduced. In a preferred embodiment, the pharmaceutically effective dosage of Nestorone®, irrespective of the particular dosage form, results in the absorption of from 100 to 450 µg/day by the patient. Preferably, the pharmaceutically effective dosage comprises a continuous dosage provided to the patient. In another embodiment, however, the pharmaceutically effective dosage comprises an interrupted dosage provided to the patient. Preferably, the interrupted dosage comprises three weeks on the dosage followed by one week off the dosage.

In accordance with one embodiment of the method of the present invention, the methods includes simultaneously treating a female patient with an estrogen compound. Preferably, the estrogen compounds comprises estradiol, and in a preferred embodiment the amount of estradiol is sufficient to provide from about 10 to 150 µg/day absorbed by the patient.

In accordance with another embodiment of the method of the present invention, the pharmaceutically effective dosage of the progestin compound comprises a transdermal dosage form.

In accordance with another embodiment of the method of the present invention, the progestin compound is selected from the group consisting of Nestorone®, 18-methyl Nestorone®, nomegestrol acetate, trimegestone, norgestimate, dienogest, drospirenone, chlormadinone acetate, promegestone, retroprogesterone, and 17-hydroxyprogesterone. In a preferred embodiment, the progestin compound comprises nomegestrol acetate, and the pharmaceutically effective dosage comprises from 2.5 to 5 mg/day. In another embodiment, the progestin compound comprises trimegestone, and the pharmaceutically effective dosage comprises from about 0.5 to 1 mg/day. In accordance with another embodiment, the progestin compound comprises dienogest, and the pharmaceutically effective dosage comprises from about 2 to 3 mg/day. In accordance with another embodiment, the progestin compound comprises drospirenone, and the pharmaceutically effective dosage comprises about 3 mg/day. In another embodiment, the progestin compound comprises chlormadinone acetate, and the pharmaceutically acceptable dosage comprises about 5 mg/day.

In accordance with another embodiment of the method of the present invention, the treating comprises providing the predetermined dosage in a transdermal form selected from the group consisting of transdermal gels, transdermal solutions, transdermal sprays, and transdermal patches. In another embodiment, the method comprises providing the predetermined dosage in a transdermal form selected from the group consisting of intravaginal tablets, intravaginal gels, and intravaginal rings. In another embodiment of the method of the present invention, the treating may comprise any form of administration previously shown to be efficient for steroid compounds including providing the predetermined dosage in the form of a nasal spray.

In accordance with another embodiment of the method of the present invention, the method includes treating comprising a subcutaneous implant.

In accordance with the present invention, a method is provided for treating neurodegeneration in post-menopausal women comprising treating the post-menopausal women with a pharmaceutically effective dosage of a progestin compound which exerts binding to progesterone receptors and elicits progesterone-receptor-induced biological responses without interacting with the androgen receptor and without inducing androgenic or glucocorticoid biological responses at a dosage sufficient to prevent or reduce neurodegeneration in the post-menopausal women, and simultaneously providing a predetermined dosage of natural estradiol In the preferred embodiment of this method of the present invention, the progestin compound comprises Nestorone®, and preferably is provided in an amount sufficient to provide between about 100 and 450 µg/day absorbed by the patient. In a preferred embodiment, the estradiol is provided in amounts sufficient to provide from about 10 to 150 µg/day absorbed by the patient.

In one embodiment of this method of the present invention, the pharmaceutically effective dosage of the progestin compound comprises a transdermal dosage form selected from the group consisting of transdermal gels, transdermal solutions, transdermal sprays, transdermal patches, intravaginal tablets, intravaginal gels, and intravaginal rings, or in another embodiment, in the form of a nasal spray.

In accordance with the present invention, a method is provided for treating neurodegeneration exhibited in a condition selected from the group consisting of multiple sclerosis, Alzheimer's disease, Parkinson's disease, and stroke in a patient comprising treating the patient with a pharmaceutically effective dosage of a progestin compound which exerts binding to progesterone receptors and elicits progesterone receptor-induced biological responses without interacting with the androgen receptor and without inducing androgenic or glucocorticoid biological responses wherein the pharmaceutically effective dosage comprises 5 mg/day or less, whereby neurodegeneration is prevented or reduced thereby. Preferably, the progestin compound comprises Nestorone®. In another embodiment, the progestin compound is selected from the group consisting of 18-methyl Nestorone®, nomegestrol acetate, trimegestone, norgestimate, dienogest, drospirenone, chlormadinone acetate, promegestone, retroprogesterone, and 17-hydroxyprogesterone.

In accordance with the present invention, a method is provided for treating ischemic damage in a patient comprising treating the patient with a pharmaceutically effective dosage of a progestin compound which exerts binding to progesterone receptors and elicits progesterone-receptor-induced biological responses without interacting with the androgen receptor and without inducing androgen or glucocorticoid biological responses, the pharmaceutically effective dosage comprising a sufficient amount of the progestin compound to reduce the total infarct volume. Any such reduction in the exterior of the infarct (ischemic change) will thus be beneficial to a stroke patient, for example. In preferred embodiments, the reduction in total infarct volume will be at least about 32% (P<0.01), preferably between about 30% and 60%, and most preferably by at least about 50%; and/or a sufficient amount of the progestin compound to reduce the ischemic lesions in the cerebral cortex, in this case preferably by at least about 22% (P<0.01), preferably between about 20% and 60%, most preferably at least about 40%; and/or a sufficient amount of the progestin compound to reduce the ischemic lesions in the subcortical structures, in this case preferably by at least about 52% (P<0.01), preferably between about 30% and 70%, and most preferably by at least about 50%. Furthermore, treatment with these progestins compounds, most preferably Nestorone®, may reduce an infarct zone after a stroke within a period of about 6 hours of that event, by at least about 30%, and preferably between at least about 30% and 60%, and most preferably at least about 50%. Furthermore, treatment with these progestin compounds, and most preferably Nestorone®, for moderate traumatic brain injury, with administration of therapeutic levels, has been found to reduce the area of brain damage by about the same amount as in the case of stroke; namely, within about 6 hours of the event by at least about 30%, preferably between about 20% and 60%, and most preferably about 50%, and to further induce neuroregeneration in order to repair the injured area of the brain.

In accordance with one embodiment of this method of the present invention, the pharmaceutically effective dosage, particularly with respect to treatment with Nestorone®, comprises from about 0.03 to 1.0 mg/day, and preferably from about 100 to 800 µg/day of the drug actually absorbed by the patient, irrespective of the dosages taken orally or otherwise.

The precise amounts of the pharmaceutically effective dosage which is desirably actually absorbed by the patient will vary, both in view of the sex of the patient and the particular method of administration. Thus, the broad ranges set forth above will comprise the amount absorbed in various delivery forms and for both males and females. Within that range, for females, using a vaginal ring, for example, the optimum dosage would be about 200 µg/day (e.g., from about 150-350 µg/day), and using a transdermal gel, the optimum dosage would be about 300 µg/day (e.g., from about 250-450 µg/day). In these cases the amount of the Nestorone®, for example, in the gel would be from 2.5 to 4.5 mg, which at a 10% rate of absorption supplies these amounts to the patient. For males, on the other hand, it is contemplated that the optimum dosage for transdermal administration would be about 800 µg/day (e.g., from about 700-850 µg/day). So, once again, the amount of Nestorone®, for example, applied transdermally would be from 7 to 8.5 mg, which at a 10% rate of absorption, supplies these amounts to the patent, and for an implant delivery of this drug to a male, the optimum dosage absorbed by the male will be in the range of from 30 to 100 µg/day.

In accordance with another embodiment of this method of the present invention, the pharmaceutically effective dosage comprises a continuous dosage provided to the patient. In another embodiment, the pharmaceutically effective dosage comprises an interrupted dosage provided to the patient.

In accordance with another embodiment of the method of the present invention, the pharmaceutically effective dosage of the progestin compound comprises a transdermal dosage.

In accordance with another embodiment of the method of the present invention, the progestin compound is 16-methylene-17α-acetoxy-19-norpregn-4-ene-3,20-dione (Nestorone®), 18-methyl Nestorone®, nomegestrol acetate, trimegestone, norgestimate, dienogest, drospirenone, chlormadinone acetate, promegestone, retroprogesterone, or 17-hydroxyprogesterone.

In accordance with another embodiment of the method of the present invention, the treating comprises providing the predetermined dosage in a transdermal form. Preferably, the transdermal form includes a transdermal gel, transdermal solution, transdermal spray, or transdermal patch. In accordance with another embodiment of the method of the present invention, the treating comprises providing the predetermined dosage in the form of a nasal spray. This embodiment has a particularly preferred application in connection with treating ischemic changes such as from strokes or TBI.

In accordance with another embodiment of the method of the present invention, the method of treating comprises a subcutaneous implant.

In accordance with the present invention, preliminary studies in tissue culture and animal models have shown that a particular class of progestin compounds, which includes Nestorone® (NES), a synthetic progestin derived from 19-norprogesterone, with no androgenic, estrogenic, or glucocorticoid actions, have been shown to have greater beneficial effects on remyelination in in vitro and in vivo models as compared, for example, to progesterone, as well as to certain other progestin compounds. There are bioassays comparing the effects of different progestins. Nestorone® has no androgenic or estrogenic action at all and also does not elicit a glucocorticoid effect except at doses 2.000-fold the therapeutic dose. The other progestins such as levonorgestrel and MPA induce androgenic responses, MPA induces both androgenic and glucocorticoid responses, and norethynodrel and norethisterone exert androgenic and estrogenic responses. Furthermore, in recent studies, NES has also been shown to stimulate proliferation of neural progenitor cells, again even higher than progesterone itself. These results have led to the discovery of a method for treating neurodegeneration in a patient comprising treating the patient with a predetermined dosage of a progestin compound which exerts binding to progesterone receptors and elicits progesterone-receptor-induced biological responses without interacting with the androgen receptor and without inducing any androgenic or glucocorticoid biological responses at a dosage sufficient to prevent or reduce neurodegeneration. In connection with this embodiment, the patient can comprise a male or female patient. In addition, in accordance with the present invention, a method for treating neurodegeneration in a patient comprises treating the patient with a pharmaceutically effective dosage of a progestin compound which exerts binding to progesterone receptors and elicits progesterone-receptor-induced biological responses without interacting with the androgen receptor and without inducing any androgenic or glucocorticoid biological responses at a dosage sufficient to prevent or reduce neurodegeneration, in conjunction with an estrogen compound. In this embodiment, the patient is preferably a female patient. The specified progestin compounds of this invention can be applied in various ways, both orally and non-orally, including gels, patches, vaginal rings for women, or the like, in a wide range of dosages, ranging broadly from as low as about 30 µg/day absorbed by the patient, such as by the use of implants or the like, up to about 5 mg/day, such as by the use of tablets or other such means of up to 3 to 5 mg. Similarly, in the case of estrogens, the amount delivered can range from as low as 1 up to about 2,000 µg per day. It is also believed that a treatment for menopausal therapy including daily doses of NES between about 100 and 450 µg/day, along with an estrogen, specifically estradiol in amounts of from 10 to 150 µg/day (absorbed doses) in gel formulations, will result in unexpectedly improved prevention or reduction in neurodegeneration and/or in myelin degeneration. This treatment can also be carried out vaginally, such as by use of a vaginal ring containing these compositions. The delivery can be either continuous or sequential, such as sequential delivery of three weeks continuous delivery followed by one week of cessation of delivery.

It has further been discovered that these treatments can not only be applied to post-menopausal women, but can be useful for the treatment in preventing or reducing neurodegeneration in conditions such as MS, AD, PD, and in connection with stroke or other causes of ischemic damage, such as TBI.

The primary focus of the present invention relates to methods for treating neurodegeneration or myelin degeneration in patients, both male and female. This primarily comprises treating these patients with pharmaceutically effective dosages of specific progestins such as Nestorone®, at dosage levels of 100 to 450 μg/day and up to 800 μg/day or less in order to prevent or reduce neurodegeneration.

In one embodiment of the present invention, however, the invention is directed specifically towards female patients. In one aspect of this treatment, the progestin is combined with an estrogen compound, such as estradiol, so that in general both prevention or reduction in neurodegeneration and/or myelin repair is effected along with either contraception or hormone therapy. Thus, in connection with young pre-menopausal women of fertile age, with or without neurodegenerative conditions such as MS, AD, PD, stroke, or the like, contraception is ensured, while in post-menopausal women, again with or without these neurodegenerative disorders, hormone therapy treatment can also be effected. Thus, in addition to contraception and/or hormone therapy treatments, these combinations of compositions can be used to prevent or reduce relapses in MS in women either of reproductive age or post-menopausally or during the post-partum period.

In a preferred embodiment, this is accomplished by administering a progestin, such as those discussed above, preferably Nestorone®, and most preferably in the form of a vaginal ring to administer this composition in the form of the specific daily doses discussed above.

In the case of post-menopausal women, in one embodiment of the present invention, compounds of this invention are administered in the form of a transdermal gel, once again preferably including the combination of both the progestin, such as Nestorone®, and estradiol. It is thus anticipated that this method can prevent or treat neurodegeneration in clinical situations of these medical conditions such as MS, AD, PD, and stroke. Preferably, the daily doses of the progestin, such as Nestorone®, will range from 100 to 450 μg/day, again with or without associated estrogen therapy in such post-menopausal women. The progestin dosages can be administered either continuously or interrupted by sequences of no treatment in order to allow for full efficacy in neuroproliferation and to induce endometrial shedding.

On the other hand, in connection with the treatment of young pre-menopausal women of fertile age, in one embodiment the present invention provides continuous long-term administration of the progestin, such as Nestorone®, at daily dosage rates of about 200 μg/day, preferably in the form of a vaginal ring. Again, this both insures contraception with or without treatment of neurodegenerative conditions such as MS and the like. Furthermore, in view of the potent anti-ovulatory action of compounds such as Nestorone® itself, the long-term administration of these dosages is adapted to prevent pregnancies as well as to prevent relapses from MS. Thus, in accordance with this invention, a new contraceptive agent is disclosed which has additional health benefits as opposed to all of the current estrogen-progestin contraceptives which do not contain these progestins with neuroprotective properties to be used in most women.

In accordance with a preferred embodiment of one aspect of the present invention, a composition is provided which includes a daily dose of Nestorone® for transdermal application, preferably in the form of a gel, containing between about 1 mg and 4.5 mg of transdermally applied Nestorone® (absorption of 10% resulting in about 100 to 450 μg/day of Nestorone®) which can be given alone, or which can be combined, preferably before use, for menopausal therapy, with estradiol, transdermally applied at from 0.5 to 1.5 mg, or 50 to 150 μg/day. In a preferred embodiment in which a vaginal ring is employed, the daily dose of Nestorone® is between about 100 and 300 μg/day either alone, or in combination with estradiol, preferably at doses of between 10 and 50 μg/day. In this embodiment these dosages can be applied either continuously, or sequentially, such as on a regimen of three weeks on and one week off.

In accordance with another embodiment of the present invention, post-menopausal women, with or without neurodegenerative disorders, can be treated to induce neural progenitor cell proliferation by providing daily dosage units comprising the progestins discussed above, including Nestorone®, in dosage amounts sufficient to induce neural progenitor cell proliferation.

The present invention also clearly has a general application for both males and females specifically for treating neurodegeneration or myelin degeneration in a patient. This method thus includes treating the patient with a pharmaceutically effective dosage, preferably 5 mg/day or less, of the progestins of the present invention so as to prevent or reduce neurodegeneration. However, in the case of the most preferred progestin, namely, Nestorone®, in view of its considerably higher potency, the amount of Nestorone® utilized will constitute a daily dose of from between 100 to 300 μg/day, preferably about 200 μg/day.

The method of administering these doses of progestins, such as Nestorone®, for example, can comprise non-oral administration. Non-oral administration can include transdermal administration by means of gels, transdermal or nasal sprays, transdermal patches, or in the form of vaginal rings or implants. Oral administration of the progestins of the present invention which are orally active, can take place in the form of tablets, capsules, cachets, dragées, pills, pellets, granules, powder, solutions, emulsions, suspensions, and the like.

As for the specific progestin compounds which can be used in accordance with this invention, these can include progestins such as Nestorone®, as well as 18-methyl Nestorone®, nomegestrol acetate, trimegestone, as well as non-androgenic progestins, such as norgestimate, dienogest, drospirenone, chlormadinone acetate, promegestone, retroprogesterone, and 17-hydroxyprogesterone. In general, the method of the present invention can thus be utilized for the prevention or reduction of neurodegeneration and/or for myelin degeneration, and/or for the treatment of conditions such as MS, AD, PD, or for the treatment of ischemic damage, such as that caused by stroke or TBI.

As for the embodiment of the present invention in which a progestin compound which exerts binding to progesterone receptors and elicits progesterone-receptor-induced biological responses without interfering with the androgen receptor and without inducing androgen or glucorticoid biological responses, it has been found that treatment with such compounds (progesterone and Nestorone®) after an incident such as a stroke, significantly increases the neuronal density in the infarct as well as in the penumbra, and decreases neuroinflammatory responses, reflected by reduced microglial density in the penumbra. Progesterone has thus been shown to be efficient at a dose of 8 mg/Kg whereas a 100-times lower dose of Nestorone® (0.08 mg/Kg) showed similar neuroprotective efficacy.

As discussed above, the daily dose of the progestins in accordance with the present invention is selected in order to exert binding to progesterone receptors and to elicit progesterone-induced biological responses without inducing either androgenic or glucocorticoid biological responses.

In accordance with a preferred embodiment of the present invention, a new contraceptive agent is provided with additional health benefits, as opposed to all current estro-progestin contraceptives, which do not contain such progestin with neuroprotective properties, to be used in most women.

BRIEF DESCRIPTION OF THE DRAWINGS

FIG. 3 is a graphical representation of the effect of progestins on the proliferation of progenitor cells;

FIG. 4 is a graphical representation of various progestins on the proliferation of progenitor cells;

FIG. 5 is a graphical representation of various progestins regarding neuroprotective efficacy;

FIG. 8A is a graphical representation comparing NPC proliferation in cell viability with various progestins;

FIG. 8C is a graphical representation comparing NPC proliferation in cell viability with various progestins;

FIG. 10 is a graphical representation demonstrating neuronal density in the infarct, penumbra, and contralateral hemisphere 48 hours after middle cerebral artery occlusion (MCAO);

FIG. 13 is a graphical representation of decreased microglial density in the penumbra subsequent to administration of progesterone and Nestorone®;

FIG. 15 is a graphical representation of neuron viability in the penumbra 48 hours after MCAO based on administration of progestin or Nestorone®;

FIG. 18 is a graphical representation of microglia in the penumbra 48 hours after MCAO based on administration of progesterone or Nestorone®.

DETAILED DESCRIPTION

Figure 1:
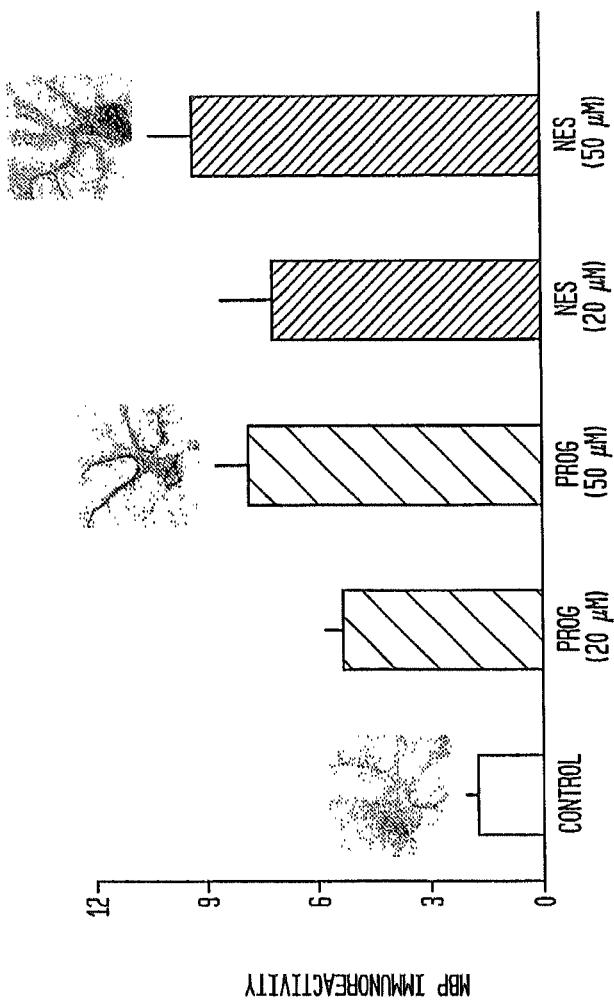
FIG. 1 is a graphical representation comparing Nestorone® with progesterone and promoting dose-dependent myelination.

The present invention is most particularly based upon the discovery of the particular properties of certain progestins. Most particularly, these progestin compounds exert binding to progesterone receptors and elicit progesterone-receptor-induced biological responses without interacting with the androgen receptor and without inducing their androgenic or glucocorticoid biological responses at a dosage sufficient to prevent or reduce neurodegeneration, and which dosage is nevertheless 5 mg/day or less in the case of oral administration, such as in the form of tablets, capsules, and the like. These progestins thus include Nestorone®, 18-methyl Nestorone®, nomegestrol acetate, trimegestone, norgestimate, dienogest, drospirenone, chlormadinone acetate, promegestone, retroprogesterone, and 17-hydroxyprogesterone. Thus, this class of progestins excludes progesterone and levonorgestrel, which interacts with the androgen receptor, and which (for progesterone) require a dosage of greater than 5 mg/day, and generally for progesterone up to 10 mg/day or more, for efficacy. The progestin compounds of the present invention can also include progestin compounds which exert binding to progesterone receptors and elicit progesterone-receptor-induced biological responses without inducing their androgenic or glucocorticoid biological responses.

We have set forth herein some presently preferred dosages for the progestins, such as Nestorone®, which is highly preferred for use in connection with the present invention. It is, however, within the skill of those in the pharmaceutical art to determine with routine experimentation what dosage of each of these progestins will be needed, depending on the particular route of administration, to deliver such an effective dose. However, while there are such variations as set forth below, it has been found that all of these progestin compounds of the present invention can be effectively utilized at dosages of 5 mg/day or less, which is considerably less than effective dosages of compounds such as progesterone. It is understood that the dosage of each of these progestins compounds, such as Nestorone®, administered in vivo may be dependent on the age, sex, health and weight of the recipient, kind of concurrent treatment, if any, frequency of treatment, and the nature of the pharmaceutical effect desired. The ranges of effective doses provided herein are not intended to be limiting and represent preferred dose ranges with the overall lower dosage range of 5 mg/day or less hereof. However, the most preferred dosages within that overall range may be tailored to the individual subject, as is understood and determinable by one skilled in the relevant art. See, e.g., Berkow et al., eds., *The Merck Manual*, 16th Ed., Merck & Co., Rahway, N.J. (1992); Goodman et al., eds., *Goodman and Gilman's The Pharmacological Basis of Therapeutics*, 8th Ed., Pergamen Press Inc., Elmsford, N.Y. (1990); Katzung, *Basic and Clinical Pharmacology*, Appleton & Lang, Norwalk, Conn. (1992); *Avery's Drug Treatment Principles and Practice of Clinical Pharmacology and Therapeutics*, 3rd Ed., ADIS Press Ltd., Williams & Wilkins, Baltimore, Md. (1987); Ebadi, *Pharmacology*, Little, Brown & Co., Boston, Mass. (1985); *Remington's Pharmaceutical Services*, 17th ed., Alphonzo R. Genaro, Mack Publishing Company, Easton, Pa. (1985); which references are entirely incorporated here by reference thereto.

The dosages can be determined by a clinician using conventional dose escalation studies. It can be expected to be within the above preferred ranges. Furthermore, while this discussion has specifically referred to the highly significant progestin component of the present invention, it can, of course, also apply with equal force to the estrogen component hereof.

In addition, by the term "pharmaceutically effective" it is meant that amount which is sufficient to effect the desired changes in the subject. The amount will vary depending upon such factors as the potency of the particular drug, the desired therapeutic effect, and the time span for which the method of application is intended to provide treatment. Those skilled in the pharmaceutical arts will be able to determine both toxic levels and the minimum effective doses of the drug in accordance with standard procedures. For instance, a proper dosage form can be prepared by measuring the in vivo rate or elution of a given drug by standard analytic techniques, e.g., spectroscopic or radioimmunoassay analysis. In vitro diffusion of the drug from a delivery device of the present invention may be determined, for example, by the methods disclosed in Chien et al., *J. Pharm. Sci.*, 63, 365 (1974) or by the methods described in U.S. Pat. No. 3,710,795, the disclosures of which are incorporated by reference herein.

The applicants have discovered that these specific progestin compounds can have unexpected properties in terms of their myelination and also for the treatment of neurodegeneration, and in particular treatment of conditions such as MS, AD, PD, and for the treatment of ischemic damage such as that caused by stroke and TBI, and furthermore that these unexpected properties can be obtained in conjunction with a contraceptive action with these compounds known to be useful for that purpose.

A particular preferred use of the progestin compounds of the present invention is thus in conjunction with an estrogen compound in female subjects. By estrogen compound one of skill in this art will appreciate that the estrogen can be selected from the group consisting of estradiol, ethinyl estradiol, estradiol sulfimates, estradiol valerate, estradiol acetate, estradiol benzoate, estrone, estriol, estriol succinate, and conjugated estrogens including conjugated equine estrogens such as estrone sulfate, 17β-estradiol sulfate, 17α-estradiol sulfate, equilin sulfate, 17β-dihydroequilin sulfate, 17α-dihydroequilin sulfate, equilenine sulfate, 17β-dihydroequilenine sulfate, 17α-dihydroequilenine sulfate, estetrol, or mixtures thereof. Most preferred is estradiol.

The combination of progestins with estrogens for contraceptive purposes is widely known. Indeed, since progestins alone cannot normally be used without developing poor bleeding patterns in women, nor for postmenopausal use, it has become necessary to combine these progestins with estrogens for these purposes. Furthermore, while the primary thrust of the present invention is based upon the discovery that certain progestins as described herein possess unexpectedly superior properties in connection with neuroprotection and myelination, and the addition of an estrogen is not necessarily for assisting in that objective, it is also possible that the use of certain estrogens in combination with these progestins provides even greater unexpected results in terms of neuroprotection, or neuroregeneration and myelin repair.

In experiments conducted in organotypic neonatal rat or mouse cerebellar slice culture, progesterone accelerated axon myelination (13,14). In a study conducted in accordance with this invention, both progesterone (PROG) and Nestorone® (NES) were found to promote dose-dependent myelination, as measured by myelin basic protein (MBP) immunoreactivity. NES was found to be significantly more potent than PROG, as NES at 20 μm was as active as PROG at 50 μm (FIG. 1). It was also shown that the intracellular progesterone receptor (PR) may mediate the promyelinating actions of PROG as the treatment did not increase myelination in cerebellar slices from PR knockout mice.

Figure 2:
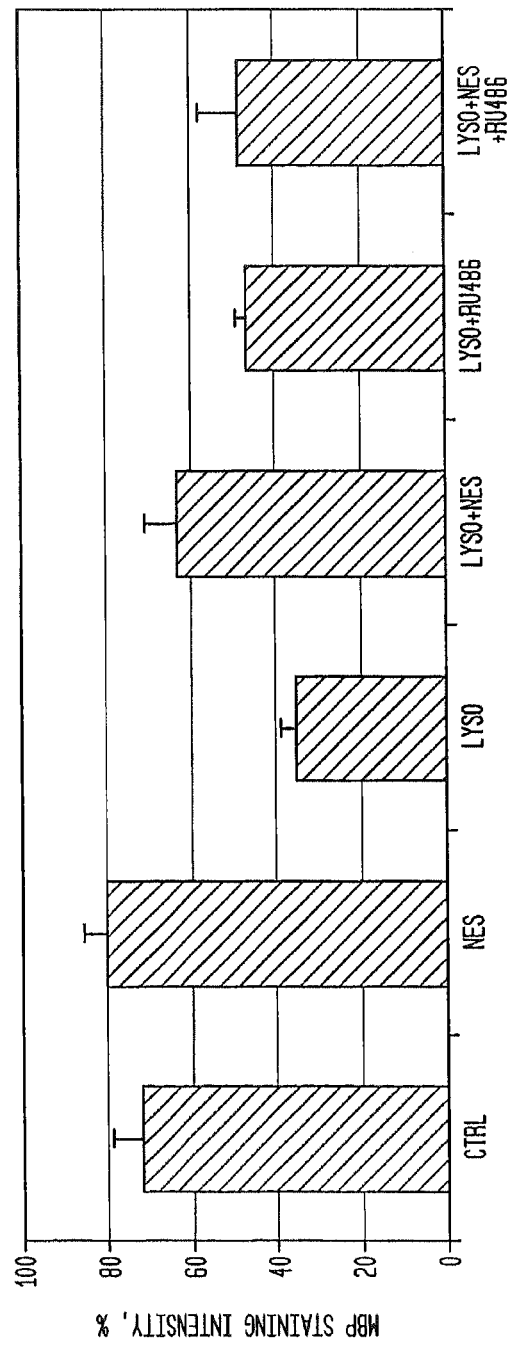
FIG. 2 is a graphical representation comparing myelination with Nestorone® lysolecithin, and RU486.
Figure 6A:
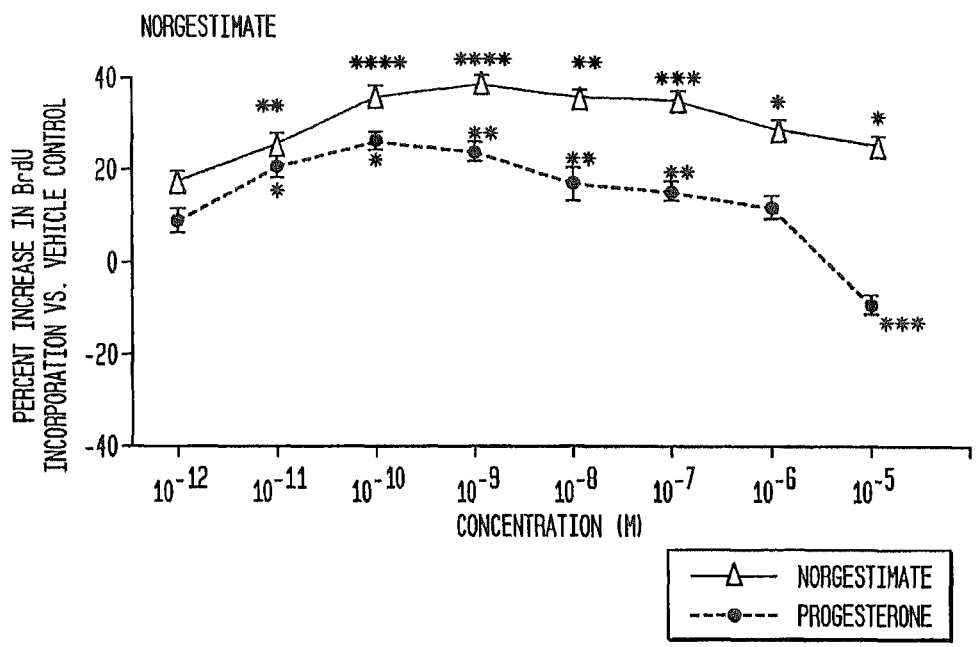
FIG. 6A is a graphical representation comparing the NPC regeneration induced by norgestimate compared with progesterone.
Figure 6B:
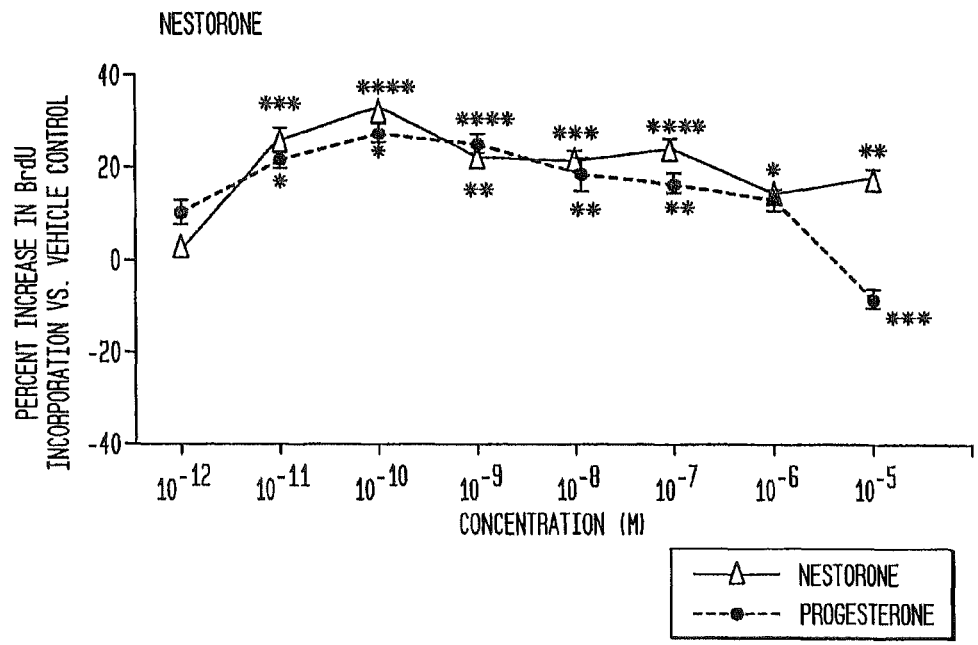
FIG. 6B is a graphical representation comparing NPC regeneration with Nestorone® compared to progesterone.
Figure 6C:
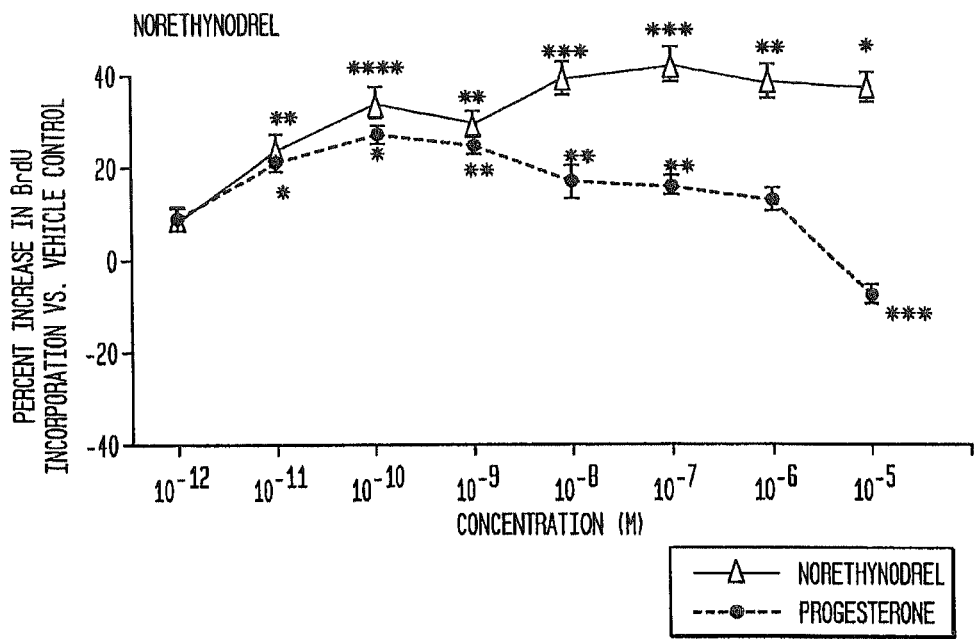
FIG. 6C is a graphical representation comparing NPC regeneration for norethynodrel compared to progesterone.
Figure 6D:
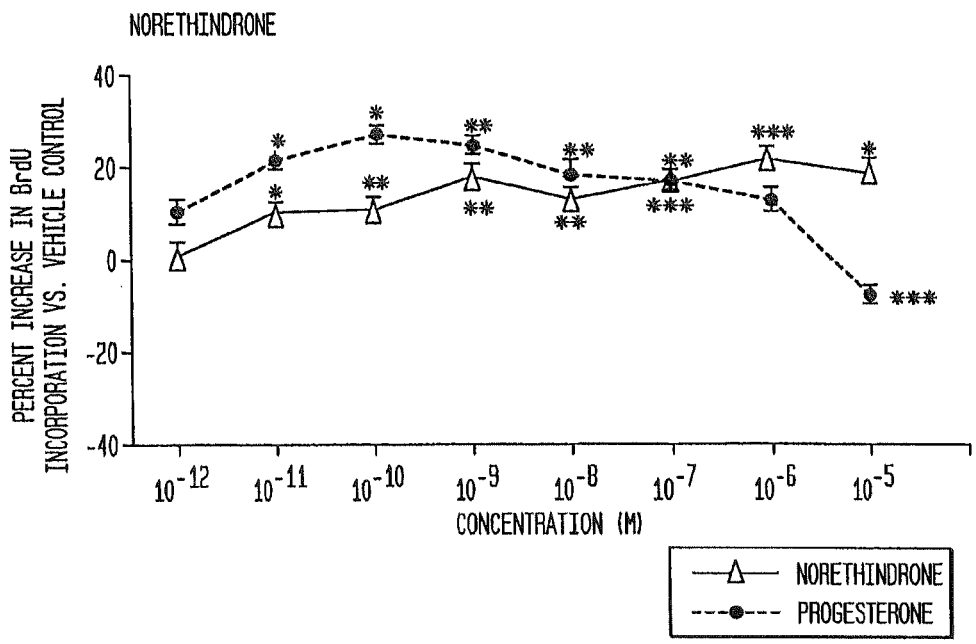
FIG. 6D is a graphical representation comparing NPC regeneration for norethindrone compared to progesterone.
Figure 7A:
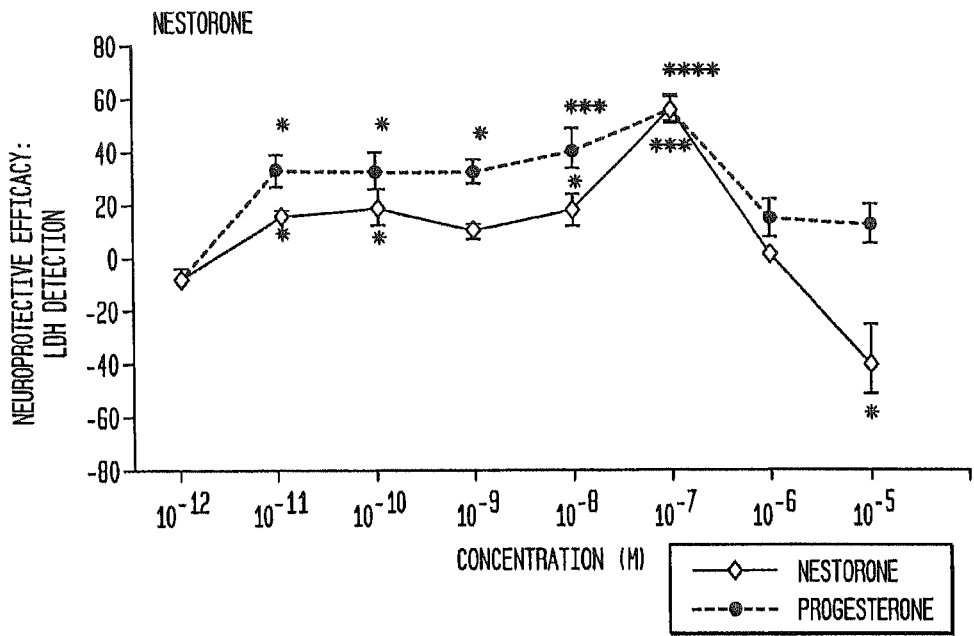
FIG. 7A is a graphical representation comparing neuroprotective efficacy for Nestorone® with progesterone.
Figure 7B:
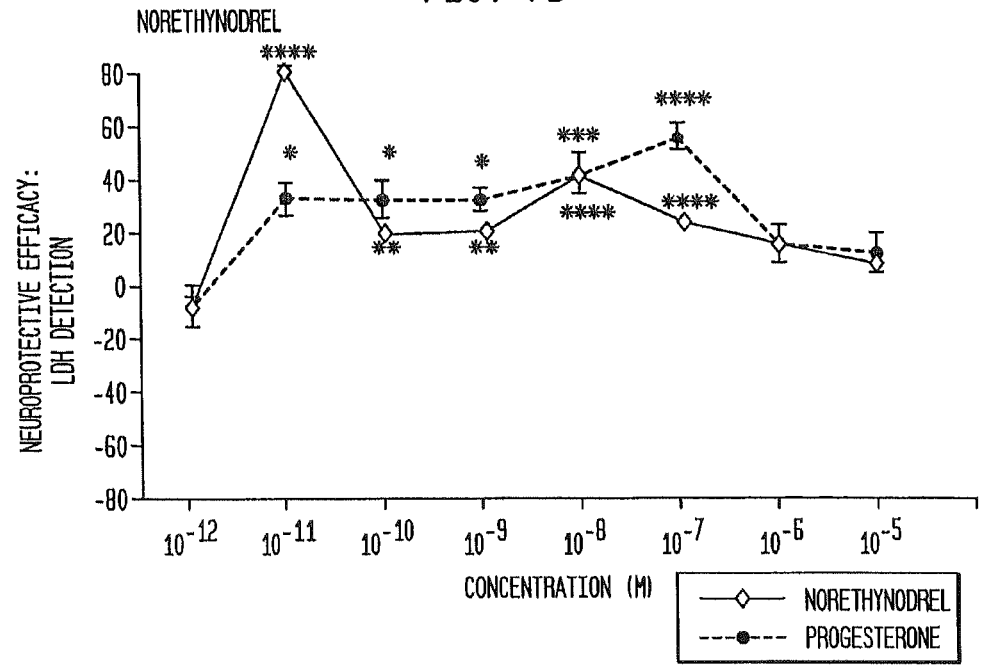
FIG. 7B is a graphical representation comparing neuroprotective efficacy for norethynodrel with progesterone.
Figure 7C:
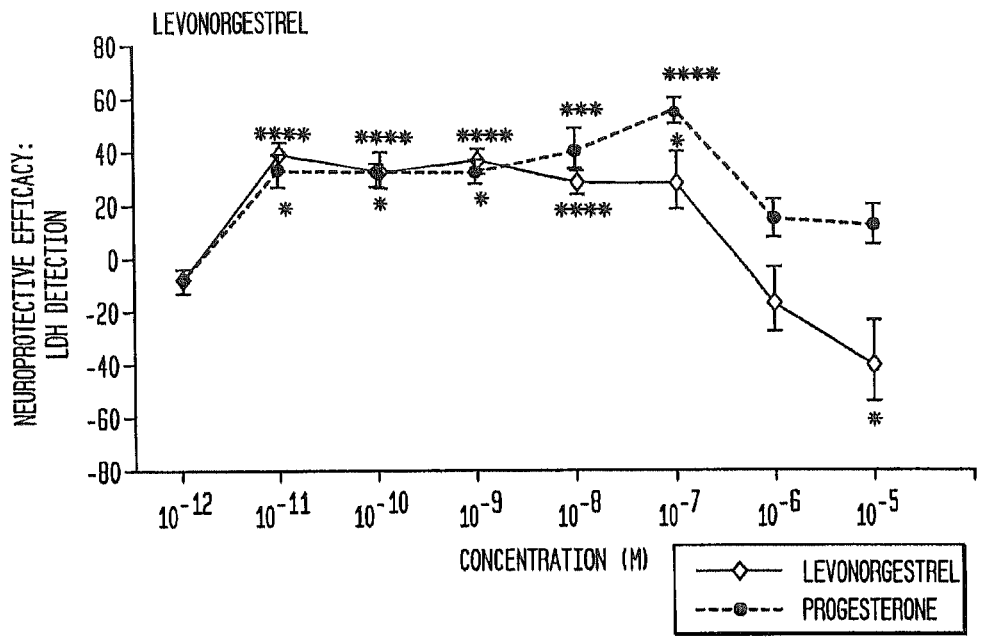
FIG. 7C is a graphical representation comparing neuroprotective efficacy for levonorgestrel with progesterone.
Figure 7D:
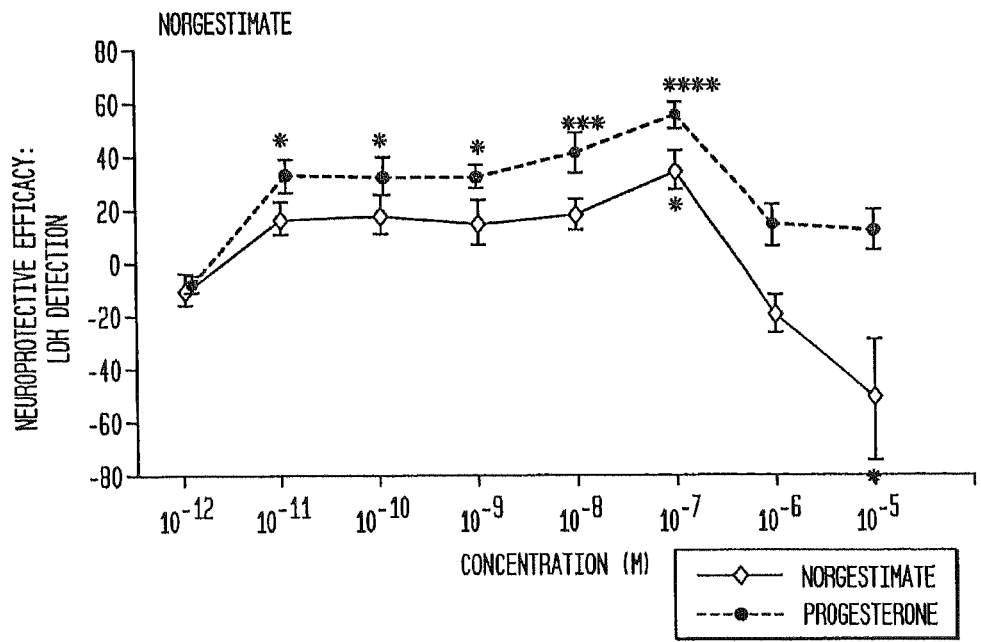
FIG. 7D is a graphical representation comparing neuroprotective efficacy for norgestimate with progesterone.
Figure 7E:
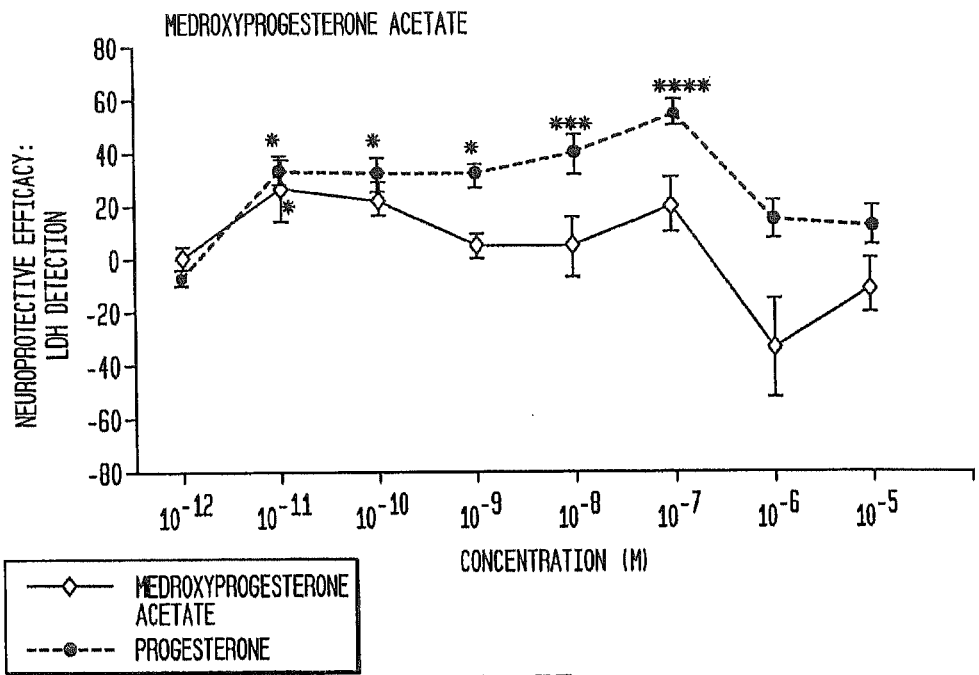
FIG. 7E is a graphical representation comparing neuroprotective efficacy for medroxyprogesterone acetate with progesterone.
Figure 7F:
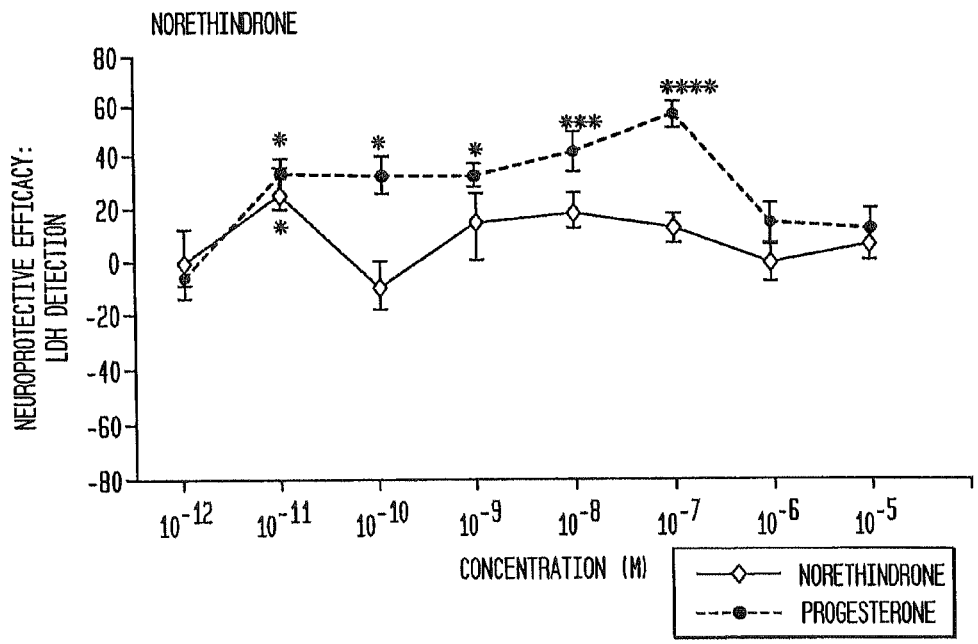
FIG. 7F is a graphical representation comparing neuroprotective efficacy for norethindrone with progesterone.

In the same animal model, cerebellar slices were cultured until myelination was complete, then incubated overnight with lysolecithin (LYSO) to produce demyelination utilizing a known technique, (15) followed by 3 days of incubation with NES 20 μM in fresh culture medium (10% penetration in slices). Slices were immunostained for MBP. As shown in FIG. 1, NES produced remyelination. MBP staining intensity was measured in cerebellar slices after completion of normal myelination, after demyelination with lysolecithin, and after 3 days of incubation with NES at 20 μm, RU486 at 10 μM, or NES+RU486. NES-stimulated remyelination of lysolecithin-demyelinated cerebellar slices may involve the classic progesterone receptor (PR), as RU486 appeared to inhibit NES activity in this model (FIG. 2).

According to the above described in vitro studies, it appears that myelination/remyelination action of NES may be mediated by the progesterone receptors (PR). Thus, NES, which is a potent agonist of PR and one of the most potent progestins without androgenic activity that induces PR-related biological responses, appears to improve myelin regeneration even better than progesterone, and this can become a treatment of the diseases or conditions associated with demyelination.

In postmenopausal women, the increase in neurodegenerative diseases has been related to the lack of estrogen and little attention has been paid to the role of progesterone. Study of the proliferation of neuronal stem cells in a rodent model showed that in the subventricular zone of the brain these cell rapidly divide and give rise to neuroblasts that will become interneurons. Progesterone increases the proliferation of these progenitor cells. Among various progestins tested for cell proliferation, Nestorone® is as effective or even more effective than progesterone. Norethynodrel and norgestimate were also more proliferative than progesterone (FIG. 3). However other progestins were either less effective than progesterone (NET, LNG) or antagonistic (MPA, NETA) on the proliferation (FIG. 4).

The effect of NES and other progestins on CNS plasticity and the neuroprotective efficacy against glutamate toxicity has also been evaluated. LDH was measured, as a well-accepted assay, to determine such effect after exposure of the cells to glutamate, and the neuronal viability was assessed under the action of various progestins. FIG. 5 shows that three progestins have comparable effect to progesterone and at 10−7M NES, and PROG exerted the higher efficacy while LNG, an androgenic progestin, was more active than PROG at lower doses.

In experiments conducted using progesterone receptor (PR) deficient mice (PR$^{-/-}$) compared with PR$^{+/-}$ and PR$^{+/+}$ mice and both progesterone and Nestorone® were administered after ischemia and reperfusion. Nestorone® was found to have at least comparable results in terms of protection against ischemic damage, but at far lower dosage levels as compared to those required for progesterone.

Example 1

In vitro studies were carried out to determine neural progenitor cell (NPC) regeneration in rats. 5-Bromo-2-deoxiuridine (BrdU) chemiluminescence enzyme-linked immunosorbant assay (ELISA) and the results are shown in FIGS. 6A-D herein. Cell proliferation was determined by S phase incorporation of BrdU. After 4 to 6 hours starvation (medium without supplements), rNPCs were loaded with 10 μM BrdU in the presence or absence of bFGF and varying concentrations of $P_4$ or test progestins in unsupplemented maintenance medium for 1d. The rNPCs were then processed as described previously (1, 14). After subtracting the value of the blank (without BrdU loading), data were analyzed using a one-way ANOVA, followed by a Neuman-Keuls post hoc test. These results demonstrate that at 24 hours norgestimate was more potent in cell proliferation than progesterone at all concentrations. Nestorone® and progesterone were comparably efficacious at their $EC_{100}$ concentrations. Norethynodrel produced comparable effects to progesterone at the low nanomolar range but was significantly more efficacious than progesterone at high nanomolar ranges. Norethindrone was less effective than progesterone and levonorgestrel and norethindrone acetate exerted minimal or no effect on proliferation while medroxyprogesterone acetate (MPA) significantly inhibited proliferation at multiple concentrations.

Example 2

Comparisons of neuroprotection against neurodegenerative insults were carried out. Efficacy was determined in connection with the protection of primary hippocampal neurons against degeneration induced by excitoxic glutamate. Hippocampal neuronal cultures grown on 90-well culture plates for 7d in vitro were pretreated with vehicle alone or test compounds, followed by exposure to 200 μM glutamate as previously described (13). After glutamate exposure, cultures were washed with HEPES-buffered saline solution and replaced with fresh NBM containing the test compounds or combinations. Cultures were returned to the incubator and incubated for 24 hours prior to analysis of neuronal viability using colorimetric LDH release in the media. Dose-response analysis was conducted for each of the progestins tested, and the results are shown in FIGS. 7A-F. Neuroprotective efficiency was calculated as follows: $NE=(V_{sample}-V_{glutamate})/(V_{subcontrol}-V_{glutamate})$. As can be seen, Nestorone® induced comparable neuroprotective efficacy to that of progesterone. Norethyndrel was more potent than progesterone at minimal effective concentrations while levonorgestrel showed comparable efficacy to progesterone. Norgestimate was found to be less potent than progesterone, as were both MPA and norethindrone.

Example 3

Figure 8B:
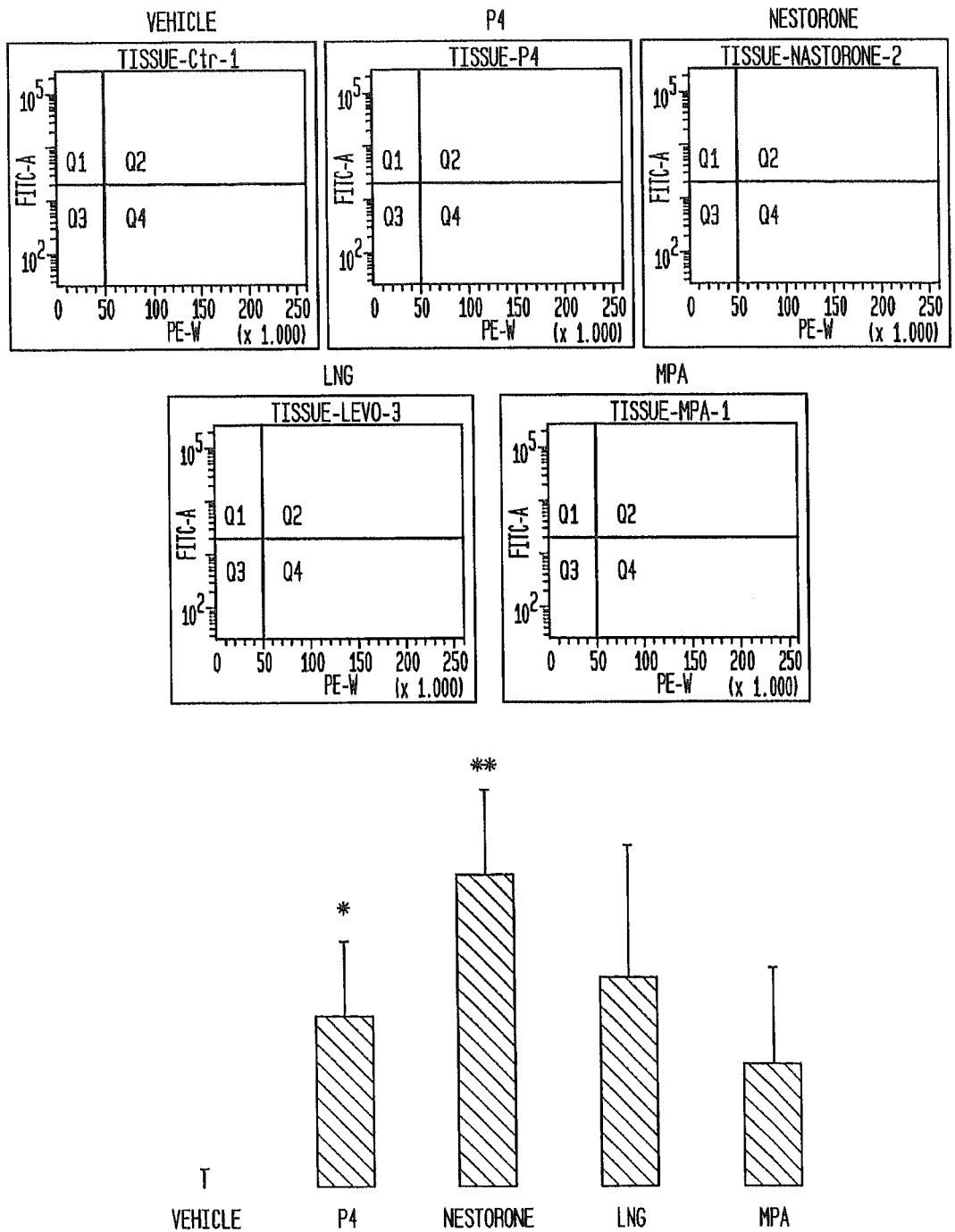
FIG. 8B is a graphical representation comparing NPC proliferation in cell viability with various progestins.

The generalized ability of the above in vitro findings to the in vivo condition were investigated. Analyses of NPC proliferation in rats and cell viability were conducted in three-month-old Sprague-Dawley ovariectomized female rats with various of the progestins. Cell cycle protein expression was determined by Western blot analysis, and the results as shown in FIG. 8A indicated that Nestorone® appeared to be slightly superior to progesterone in terms of increased PCNA expression at the protein level. Levonorgestrel and MPA, on the other hand, had no significant effect on PCNA expression, while CDC2 protein expression was significantly increased by both progesterone and Nestorone®, but not with levonorgestrel and MPA. In order to assess the total number of BrdU+ cells, the contralateral hippocampal hemisphere used for protein analysis was fixed and processed by FACS analysis. The total number of BrdU+ cells per each hippocampus was determined and normalized to that of vehicle control. The results are shown in FIG. 8B demonstrating that Nestorone® was slightly superior to progesterone in significantly increasing Brd+ cell numbers while levonorgestrel was comparable to progesterone while MPA had no significant effect on cell proliferation in vivo. In order to measure cell viability in terms of promotion of mitochondrial function and reduction in oxidative damage expression of the alpha subunit of ATP synthase-Complex V (CVα) of the mitochondrial oxidative phosphorylation pathway was assessed by Western blot analysis. The results as shown in FIG. 8C demonstrate that Nestorone® increased CVA expression even greater than progesterone and levonorgestrel while again MPA exerted no significant effect on CVα expression levels.

Example 4

The effects of various progestins on apoptosis was studied using Western blot analysis to determine the expression level of Bax, an apoptosis mediator by translation to the mitochondria to release apoptotic factors such as cytochrome c and Bcl-2. The ratio of Bax to Bcl-2 was used as an indicator of in vivo apoptotic activity. The results obtained demonstrated that both progesterone and Nestorone® had no effect on the ratio of Bax/Bcl-2 expression, while levonorgestrel and MPA significantly increased the ratio demonstrating a pro-apoptotic effect therein.

Example 5

Figure 9A:
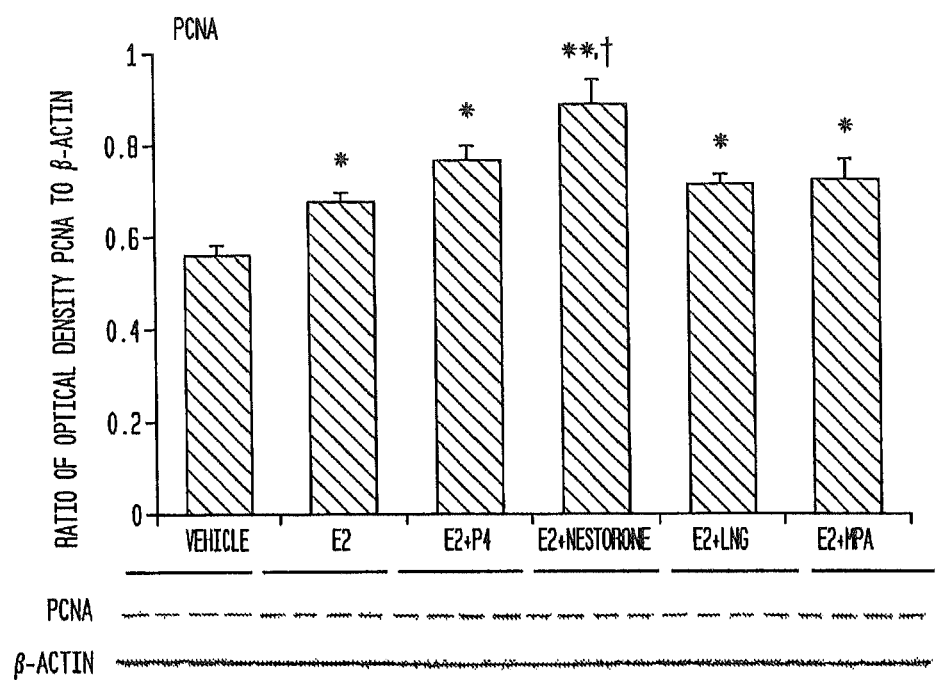
FIG. 9A is a graphical representation of PCNA expression of various progestins.

The impact of the combination of 17β-estradiol ($E_2$) and various progestins on neurogenesis and cell viability in vitro was also carried out. Young adult ovariectomized female Sprague Dawley rates were thus divided into six groups and received injection of either $E_2$ alone or $E_2$ combined with one of the progestins. Hippocampi were isolated 24 hours later for Western blot analysis and flow cytometry to determine the impact of treatment on cell viability and neurogenesis respectively. The expression level of PCNA was assessed to determine the impact of the treatment compounds on entry into the cell cycle required for neurogenesis. The results demonstrated that Nestorone® plus $E_2$ induced the greatest magnitude of PCNA expression and neural progenitor cell proliferation (see FIG. 9A).

Figure 9B:
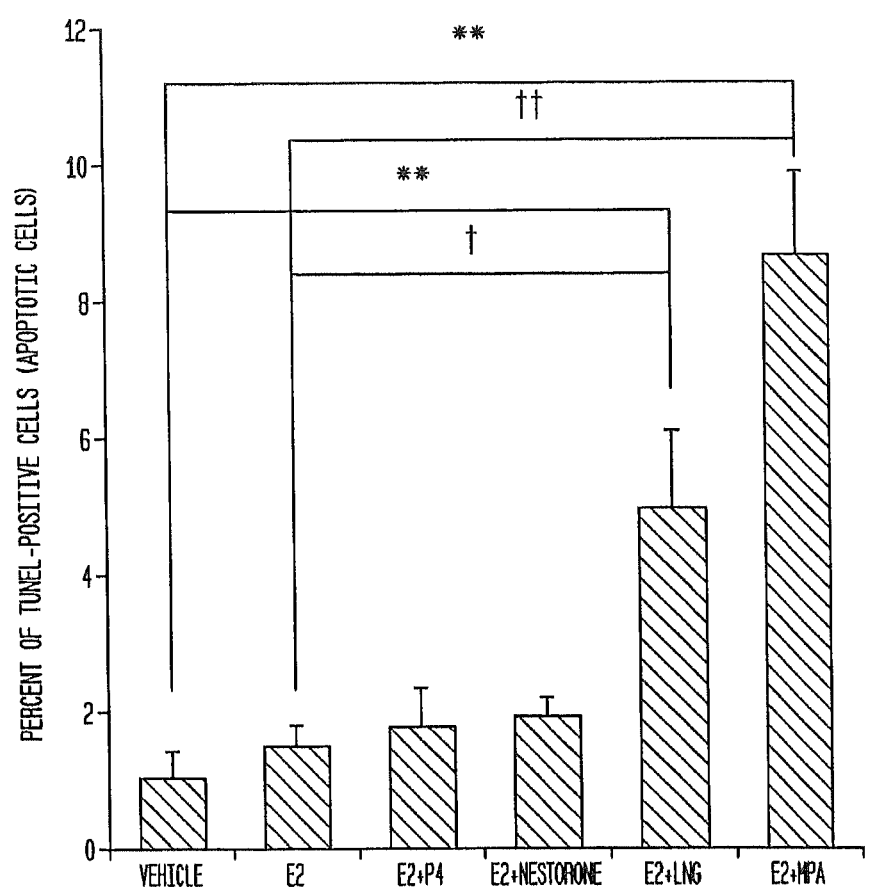
FIG. 9B is a graphical representation of percent of TUNEL-positive cells.

Importantly, Nestorone®, in combination with estradiol, did not increase neural progenitor cell death as evidenced by no increase in TUNEL positive cells, a marker for apoptosis. In contrast, both MPA and levonogestrel, in combination with estradiol, significantly increased apoptosis, as evidenced by an increase in TUNEL positive cells (see FIG. 9B). As noted above, both MPA and levonorgestrel increased cell proliferation.

Example 6

In order to test the effect of steroid treatments after reperfusion, adult male $PR^{lacz}$ mice were anesthetized and the middle cerebral artery (MCA) was occluded for one hour with an intraluminal filament. After ligature of the left common carotid artery, a nylon monofilament coated with thermo-melting glue was introduced through an arteriotomy performed on the external carotid artery and advanced into the internal carotid artery. Occlusion of the MCA was controlled by monitoring the cerebral blood flow within the MCA territory by laser Doppler flowmetry. The filament was withdrawn one hour after occlusion to allow reperfusion, and the common carotid artery ligature was also removed. The mice were randomly and blindly assigned to either progesterone, allopregnanolone or Nestorone®, or vehicle-treated (sesame oil; sigma). All of the steroids were initially dissolved in a small volume of ethanol and further diluted in sesame oil to obtain the desired final steroid concentrations. Injections were given interperitoneally (IP) at 1, 6, and 24 hours after MCA occlusion (MCAO) according to established neuroprotective protocols. Treated mice were killed at 48 hours after MCAO.

Figure 11:
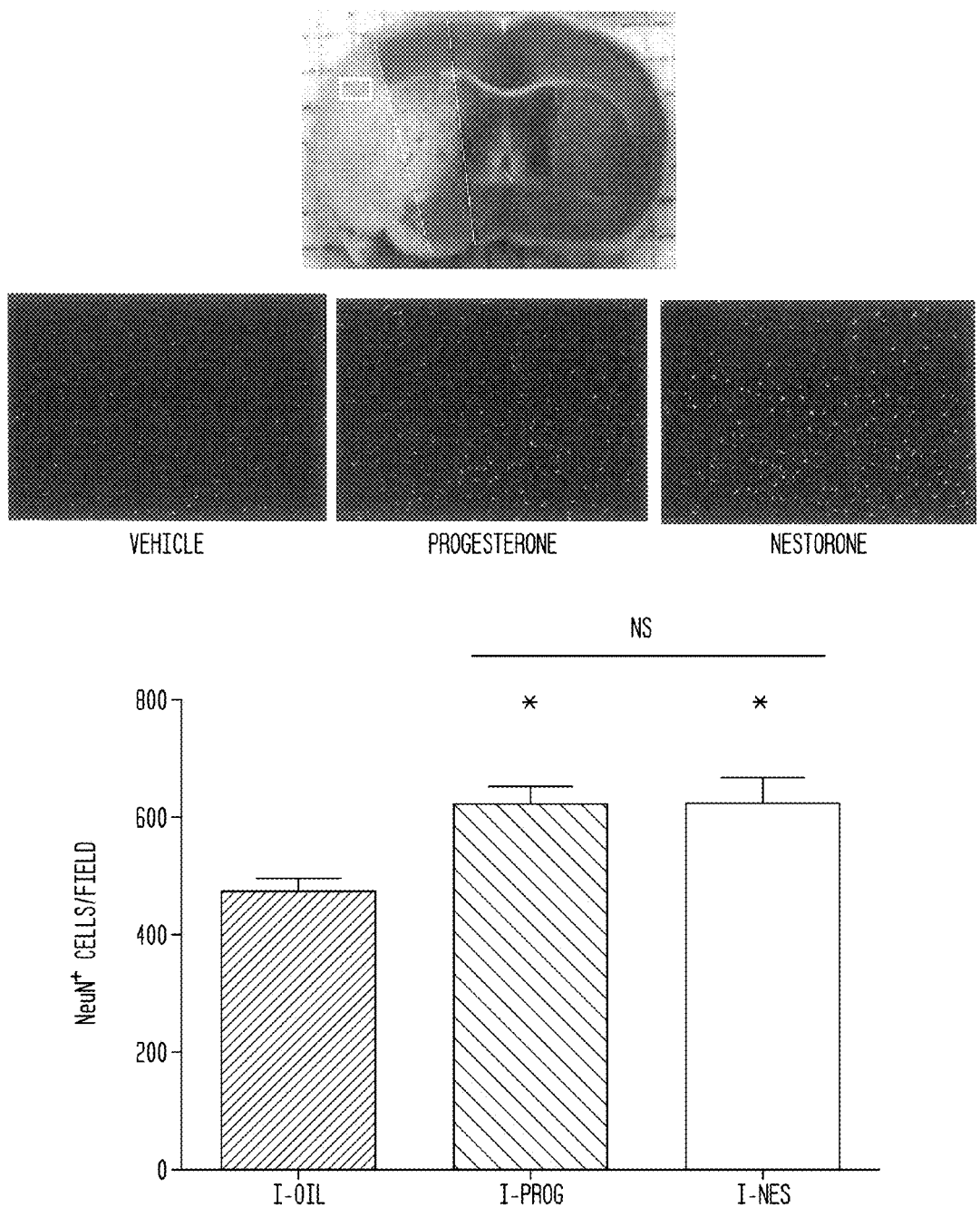
FIG. 11 is a graphical representation showing increased neuronal density of the infarct subsequent to administration of progesterone and Nestorone®.
Figure 12:
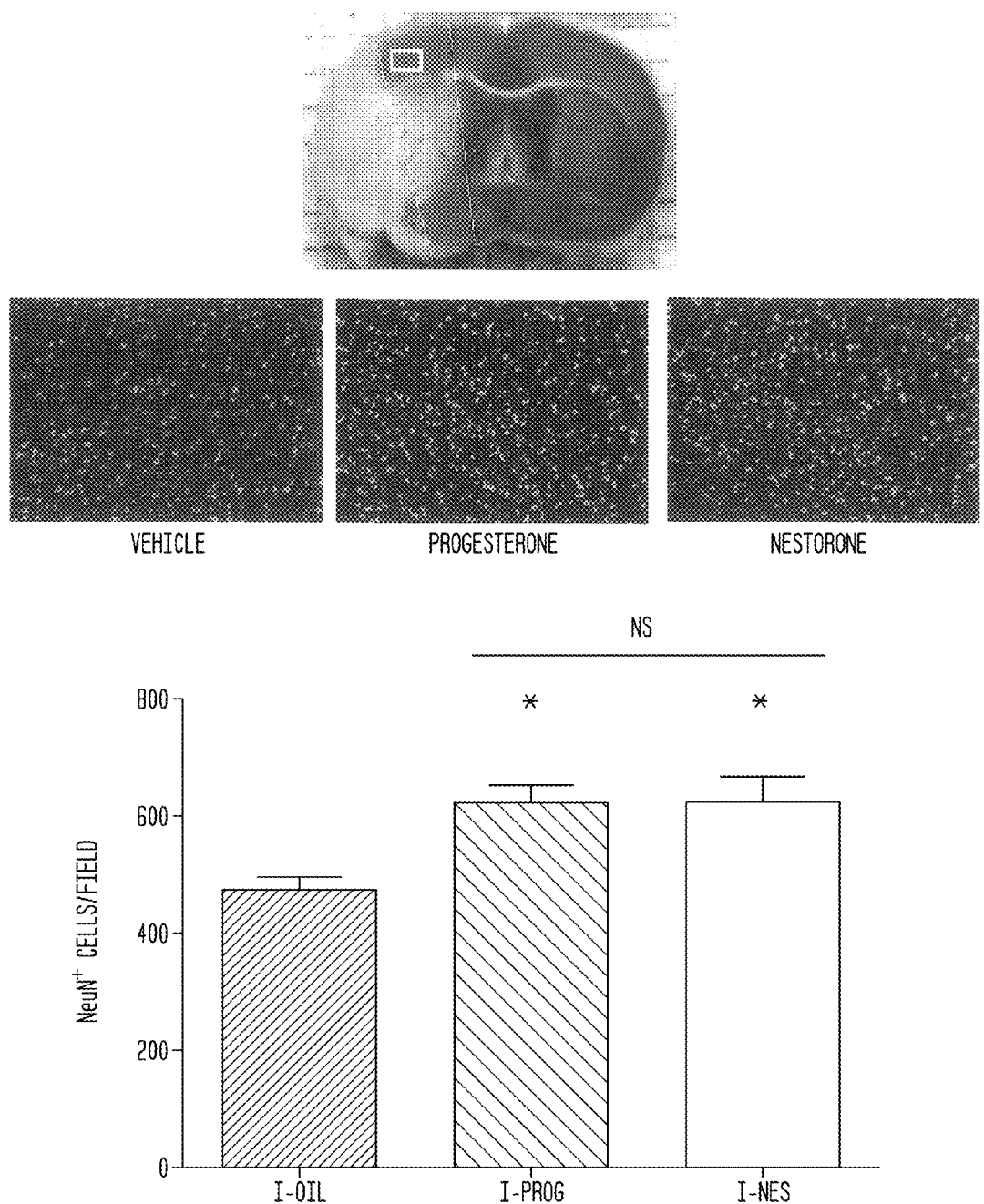
FIG. 12 is a graphical representation of increased neuronal density in the penumbra subsequent to administration of progesterone and Nestorone®.

Cerebral infarct volumes and areas were determined after triphenyltetrazolium chloride (TTC) staining of brain sections. The details of this procedure are set forth in "Progesterone Receptors: A Key For Neuroprotection In Experimental Stroke," Endocrinology, August 2012, 153(8), pp. 1-11, which is incorporated herein by reference thereto in its entirety. As shown in FIG. 10, 48 hours after MCAO the neuronal density in the infarct, the penumbra, and the contralateral hemisphere can be seen. In FIGS. 11, 12 and 13, after the administration of progesterone and Nestorone®, in neuronal density the infarct (FIG. 11) and the penumbra (FIG. 12) can clearly be shown. In FIG. 13 the decrease in microbial density in the penumbra after administration of progesterone and Nestorone® is also clearly shown.

Figure 14A:
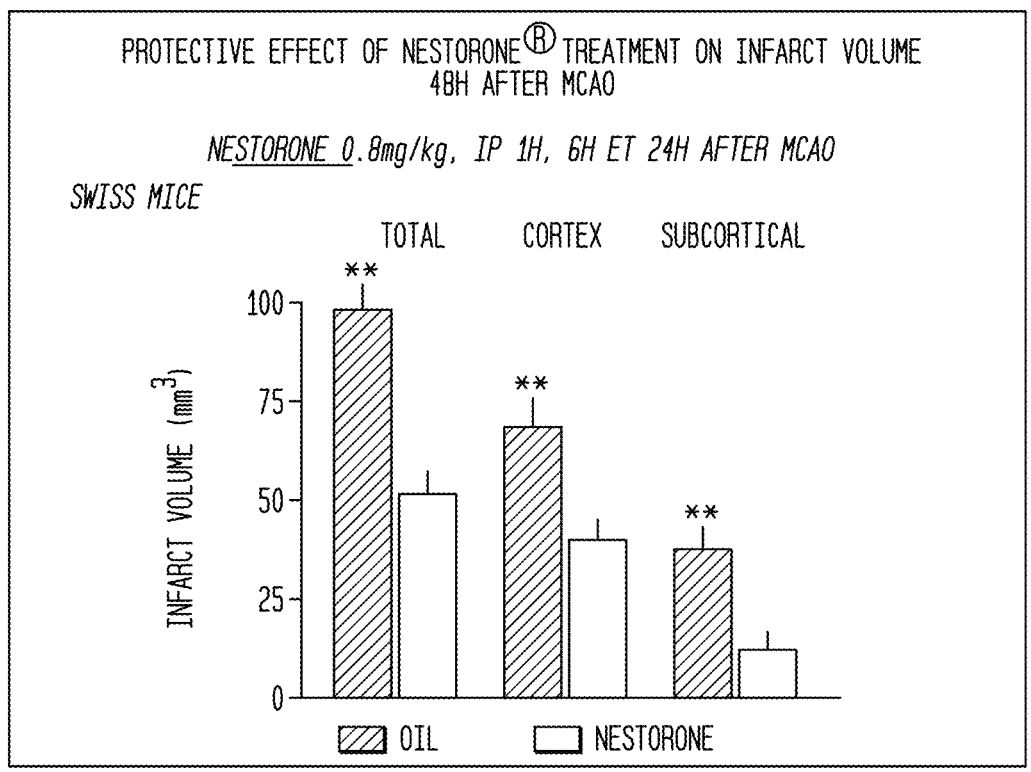
FIG. 14A is a graphical representation showing the infarct volume 48 hours after MCAO using Nestorone®.
Figure 14B:
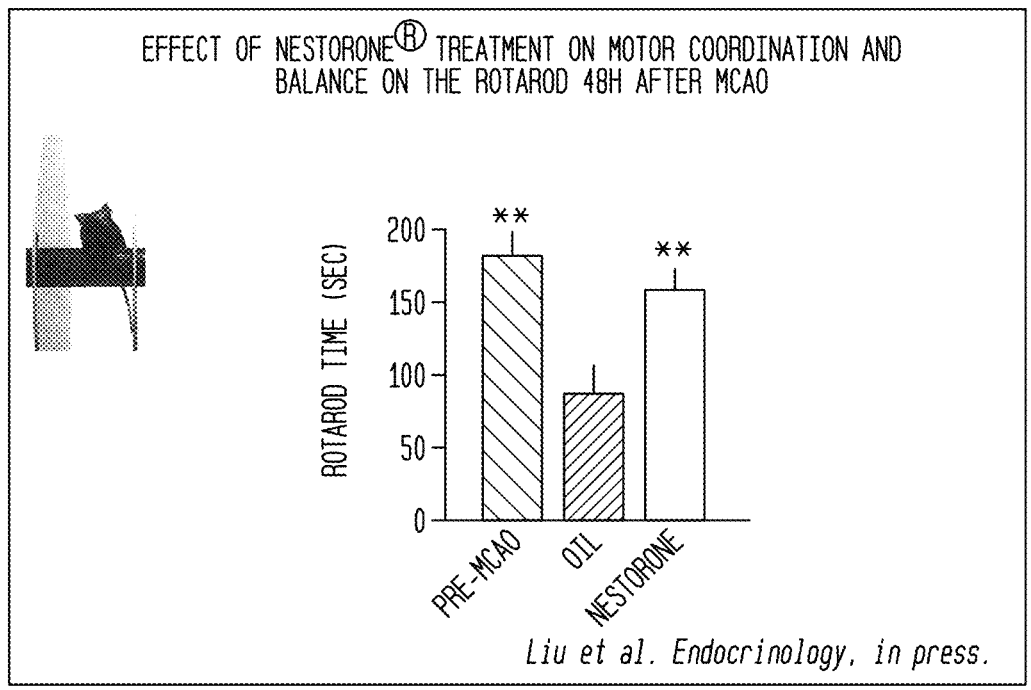
FIG. 14B is a graphical representation of motor coordination and balance 48 hours after MCAO based on application of Nestorone®.
Figure 16:
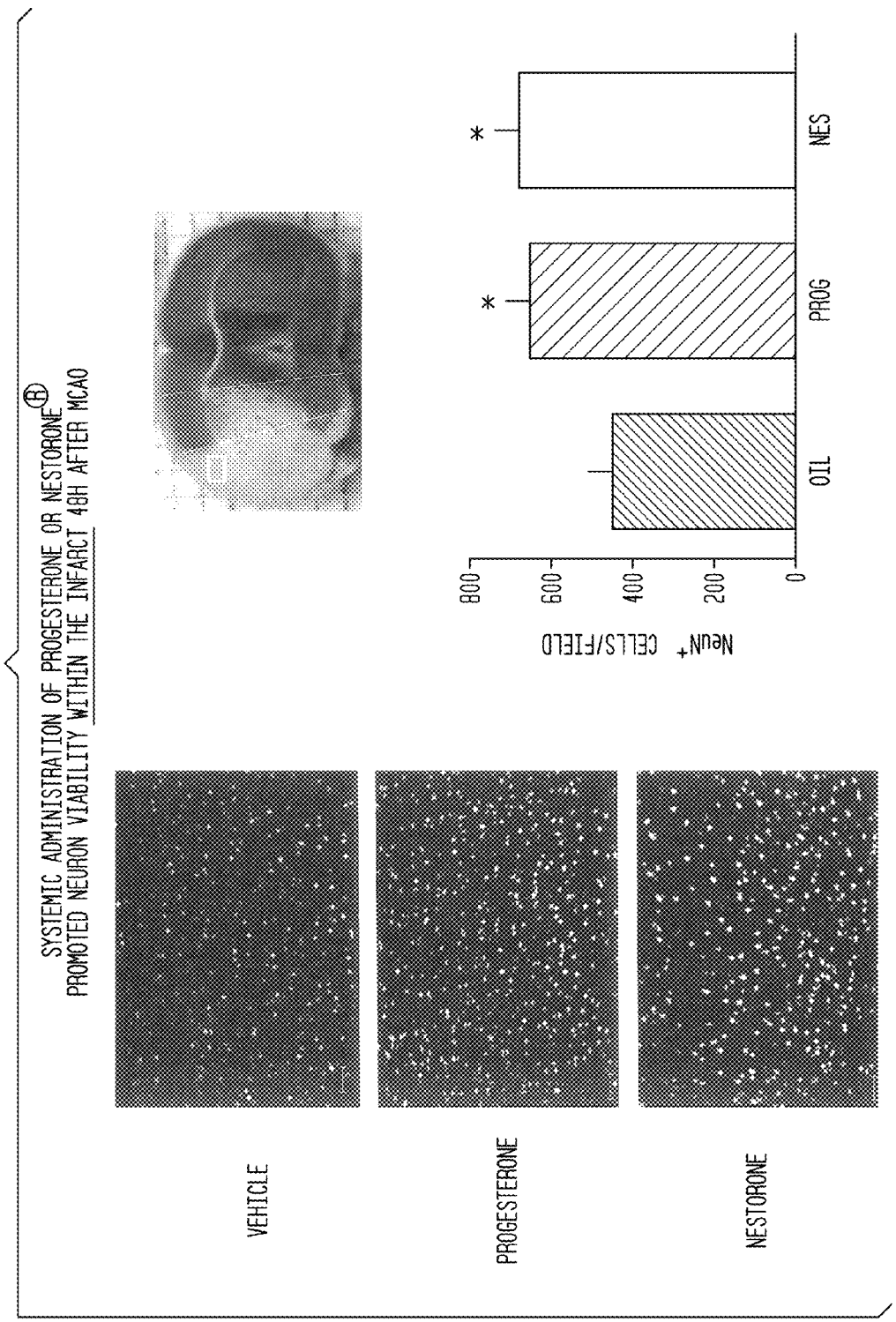
FIG. 16 is a graphical representation of neuron viability within the infarct 48 hours after MCAO based on administration of progesterone or Nestorone®.
Figure 17:
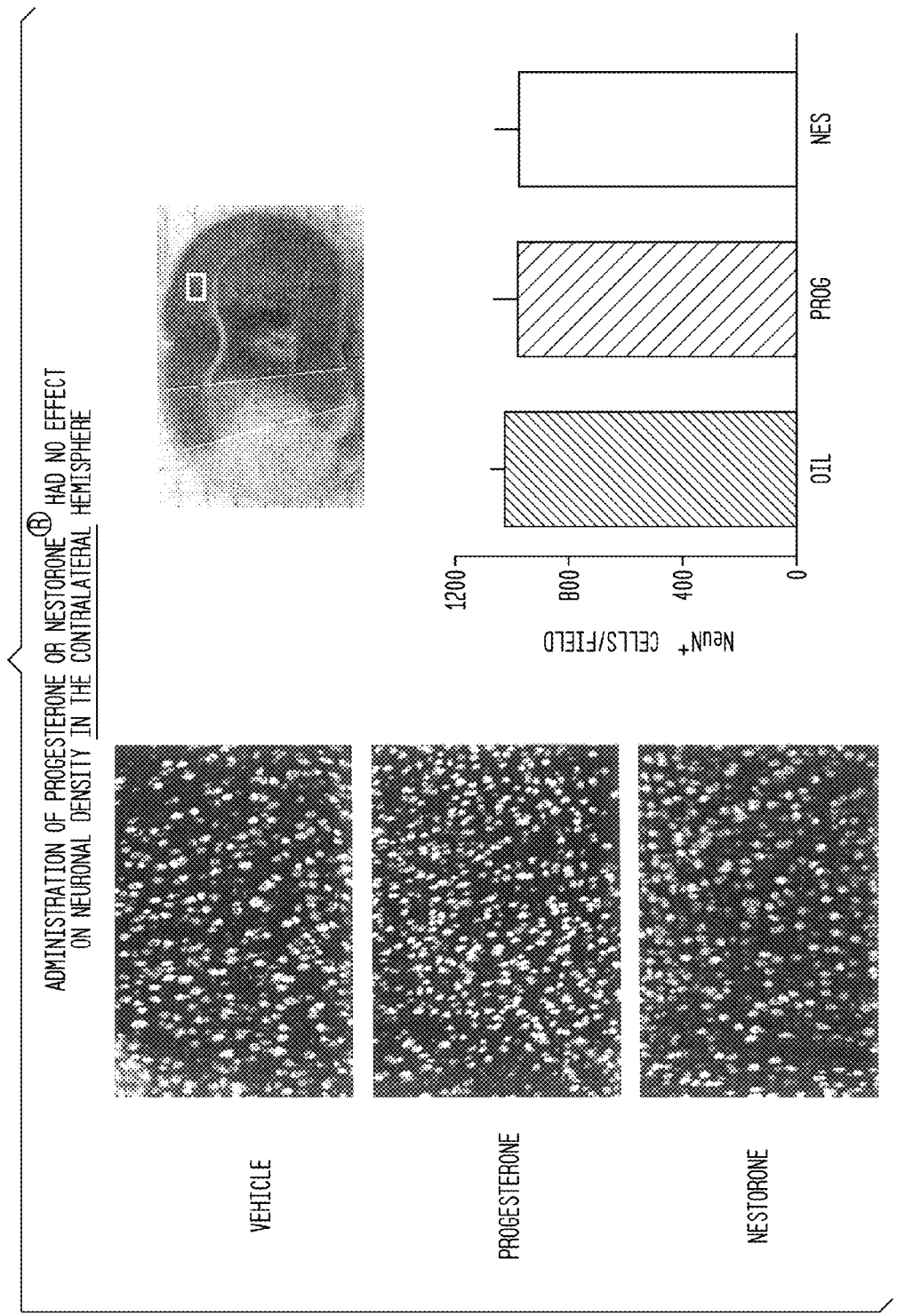
FIG. 17 is a graphical representation of neuronal density in the contralateral hemisphere based on administration of progesterone or Nestorone®.

Finally, as shown in FIGS. 14a and 14b, 48 hours after MCAO the protective effect of Nestorone® treatment on infarct volume is clearly shown in FIG. 14A, and the effect of Nestorone® treatment on motor coordination and balance on the rotarod is shown in FIG. 14B. Thus, the total infarct volume and ischemic lesions in both the cerebral cortex and subcortical structures were clearly reduced by Nestorone® treatment in PR$^{+/+}$ but not in PR$^{+/-}$ mice. Motor coordination, when assessed on the rotarod, also demonstrated significant negative correlations with the infarct volume. The Nestorone® treatments reduced the total infarct volume by 32%, the ischemic lesions in cerebral cortex and in subcortical structures, respectively, by 22% and 52%, and increased the time PR$^{+/+}$ mice remained on the rotarod by 33%. The results clearly showed the longer term neuroprotective effects from additional treatment with exogenous progestins such as Nestorone® and the significance of the presence of PR. It was further shown that Nestorone® improved neurological outcomes at a dose 100 times lower than that of progesterone.

The present invention provides a method of stimulating neuroregeneration and possibly inhibiting and reversing neurodegenerative disorders such as MS or AD, as well as stroke or TBI.

Demonstration that progesterone receptors play a key role in neuroprotection was quite unexpected, and opens the way for the use of synthetic progestins, designed to target these receptors, in neuroprotective strategies for various types of injuries, including TBI, or with regard to degenerative processes where progesterone has previously been shown to be efficient. Thus, previous studies (22) of brain injury models such as TBI suggested that progesterone might exert its neuroprotective effect via its metabolite allopregnanolone. Indeed, that progesterone may exert its neuroprotective effects via allopregnanolone was also proposed for stroke (23). Since allopregnanolone, however, does not bind to progesterone receptors, but acts by modulating GABA$_A$ receptors or mitochondrial activity, this further suggests that the progesterone receptors do not play a key role in neuroprotection.

The proposed method comprises reversing the myelin degeneration with a dose of NES in the range of about 100 to 450 µg per day administered either by a vaginal ring or in a vaginal gel alone or in association with estradiol.

In another embodiment of the invention, NES, or a progestin without androgenic or glucocorticoid properties, is administered to postmenopausal women who receive low doses of estrogen as hormone therapy and a possible prevention of neurodegeneration.

The present invention pertains to the discovery that NES is more active than progesterone to stimulate progenitor neuronal cells as well as the regeneration of myelin. A further core aspect of the invention is that agents capable of binding to the progesterone receptors and inducing PR-induced biological responses, would be effective in preventing or reversing neurodegeneration, for women in reproductive age as well as postmenopausal, women.

The term "Nestorone®" (NES) refers to a 19-norprogesterone derivative that exerts a potent progestational and antiovulatory action and does not carry androgenic or estrogenic or glucocorticoid actions at therapeutic levels (16). In particular, it refers to 16-methylene-17α-acetoxy-19-nor-pregn-4-ene-3,20-dione, which was formerly referred to as ST1435.

The term "DDU" herein refers to daily dosage units wherein the DDU is in oral formulation for other 19-norprogesterone derivatives that are active orally (not NES), or in a vaginal (gel or ring) or transdermal formulation (gel, spray), or as a nasal spray.

The term "contraceptive agent" used herein refers to medications administered in order to prevent or reduce the likelihood of pregnancy.

The present invention is based on the fact that progesterone stimulates myelin repair. These effects are mediated by progesterone receptors (PR). The present invention reveals that NES is more active than PROG and can regenerate myelin at doses that also exert contraceptive efficacy.

The present invention also reveals that progenitor cells of neuronal tissue proliferate when cultured with progesterone and moreover with NES at lower doses indicating a higher activity.

Also, progesterone and some progestins, especially NES and also norgestimate (a non-androgenic gonane) and norethynodrel (an estrane progestin with estrogenic activity) stimulate progenitor cell proliferation.

Based on the superior effect of NES on myelin stimulation as well as on neuroregeneration, it is a purpose of the present invention to improve the medical conditions of multiple sclerosis and neurodegenerative disorders and at the same time providing a contraception in women of fertile age or a hormonal therapy in women who are in the menopause.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The methods of treating neurodegeneration or myelination which are disclosed in this application are particularly useful in the form of a non-oral dosage form of a specified progestin, such as Nestorone®, either alone or in combination with an estrogen, such as estradiol. This composition is used in the form of a transdermal product, such as a gel, solution, transdermal or nasal spray, or patch, or in the form of a vaginal ring, which can thus be used by a patient to reduce neurodegeneration and when combined with the estrogen, to also be used for contraception and/or hormone replacement therapy.

REFERENCES

1. Confavreux C, Aimard G, Devic M. Course and prognosis of multiple sclerosis assessed by the computerized data processing of 349 patients. Brain 1980; 103(2):281-300
2. Confavreux C, Vukusic S. Natural history of multiple sclerosis: a unifying concept. Brain 2006; 129(Pt 3):606-16
3. Pugliatti M, Rosati G, Carton H, Riise T, Drulovic J, Vecsei L, Milanov I. The epidemiology of multiple sclerosis in Europe. Eur. J. Neurol. 2006; 13(7):700-22
4. Dutta R, Trapp B D. Pathogenesis of axonal and neuronal damage in multiple sclerosis. Neurology 2007; 68(22 Suppl 3):S22-S31
5. Kornek B, Storch M K, Weissert R, Wallstroem E, Stefferl A, Olsson T, Linington C, Schmidbauer M, Lassmann H. Multiple sclerosis and chronic autoimmune encephalomyelitis: a comparative quantitative study of axonal injury in active, inactive, and remyelinated lesions. Am. J. Pathol. 2000; 157(1):267-76
6. Patani R, Balaratnam M, Vora A, Reynolds R. Remyelination can be extensive in multiple sclerosis despite a long disease course. Neuropathol. Appl. Neurobiol. 2007; 33(3):277-87
7. Patrikios P, Stadelmann C, Kutzelnigg A, Rauschka H, Schmidbauer M, Laursen H, Sorensen P S, Bruck W, Lucchinetti C, Lassmann H. Remyelination is extensive in a subset of multiple sclerosis patients. Brain 2006; 129(Pt 12):3165-72
8. Irvine K A, Blakemore W F. Remyelination protects axons from demyelination-associated axon degeneration. Brain 2008; 131(Pt 6):1464-77
9. Confavreux C, Hutchinson M, Hours M M, Cortinovis-Tourniaire P, Moreau T. Rate of pregnancy-related relapse in multiple sclerosis. Pregnancy in Multiple Sclerosis Group. N. Engl. J. Med. 1998; 339(5):285-91
10. Holmqvist P, Wallberg M, Hammar M, Landtblom A M, Brynhildsen J. Symptoms of multiple sclerosis in women in relation to sex steroid exposure. Maturitas. 2006 May 20; 54(2):149-53
11. Nilsen J, Brinton R D. Impact of progestins on estrogen-induced neuroprotection: synergy by progesterone and 19-norprogesterone and antagonism by medroxyprogesterone acetate. Endocrinology 2002; 143(1):205-12
12. Liu L, Wang J, Zhao L, Nilsen J, McClure K, Wong K, Brinton R D. Progesterone increases rat neural progenitor cell cycle gene expression and proliferation via extracellularly regulated kinase and progesterone receptor membrane components 1 and 2. Endocrinology. 2009 July; 150(7):3186-96.
13. Ghoumari A M, Ibanez C, El Etr M, Leclerc P, Eychenne B, O'Malley B W, Baulieu E E, Schumacher M. Progesterone and its metabolites increase myelin basic protein expression in organotypic slice cultures of rat cerebellum. J. Neurochem. 2003; 86(4):848-59
14. Ghoumari A M, Baulieu E E, Schumacher M. Progesterone increases oligodendroglial cell proliferation in rat cerebellar slice cultures. Neuroscience 2005; 135(1):47-58
15. Birgbauer E, Rao T S, Webb M. Lysolecithin induces demyelination in vitro in a cerebellar slice culture system. J. Neurosci. Res. 2004; 78(2):157-66
16. Kumar N, Koide S S, Tsong Y, Sundaram K. Nestorone: a progestin with a unique pharmacological profile. Steroids 2000; 65(10-11):629-36
17. Sitruk-Ware R. New progestagens for contraceptive use. Hum. Reprod. Update. 2006; 12(2):169-78
18. Gibson L, Gray L J, Bath P M, Murphy S P (2008) Progesterone for the treatment of experimental brain injury; a systematic review. Brain 131:318-328
19. Sayeed I, Wali B, Stein D G (2007) Progesterone inhibits ischemic brain injury in a rat model of permanent middle cerebral artery occlusion. Restor. Neurosci. 24:151-159
20. Brinton R D, Thompson R F, Foy M R, Baudry M, Wang J, Finch C E, Morgan D E, Pike C J, Mack W J, Stanczyk F C, Nilsen J (2008) Progesterone receptors: form and function in the brain. Front Neuroendocrinal 29:313-339
21. Wang J M, Liu L, Irwin R W, Chen S, Brinton R D (2008) Regenerative potential of allopregnanolone. Brain Res. Rev. 57:398-409
22. Sayeed J., Parvey S., Wali B., Siemen D., Stein, D. G. (2009) Direct inhibition of the mitochondrial permeability transection pore: a possible mechanism for better neuroprotective effects of allopregnanolone over progesterone. Brain Res. 1263: 165-173.
23. Sayeed T., Guo Q., Hoffman S. W., Stein D. G. (2006) Allopregnanolone, a progesterone metabolite is more effective than progesterone in reducing cortical infarct volume after transient middle cerebral artery occlusion. Ann. Emerg. Med. 47:381-389.

The invention claimed is:

1. A method of treating ischemic damage in the cerebral cortex associated with a stroke or traumatic brain injury in a patient comprising treating said patient with a pharmaceutically effective dosage of a progestin compound which exerts binding to progesterone receptors and elicits progesterone-receptor-induced biological responses without interacting with the androgen receptor and without inducing androgen or glucocorticoid biological responses, said pharmaceutically effective dosage comprising a sufficient amount of said progestin compound to reduce the total infarct volume by at least 32%, and said progestin compound is 16-methylene-17α-acetoxy-19-norpregn-4-ene-3,20-dione.

2. The method of claim 1 wherein said pharmaceutically effective dosage comprises an amount of said progestin compound which provides from about 0.1 to 1.0 mg/day absorbed by said patient.

3. The method of claim 2 wherein said pharmaceutically effective dosage comprises an amount of said progestin which provides from about 100 to 800 µg/day absorbed by said patient.

4. The method of claim 1 wherein said pharmaceutically effective dosage comprises a continuous dosage provided to said patient.

5. The method of claim 1 wherein said pharmaceutically effective dosage comprises an interrupted dosage provided to said patient.

6. The method of claim 1 wherein said pharmaceutically effective dosage of said progestin compound comprises a transdermal dosage.

7. The method of claim 1 wherein said treating comprises providing said predetermined dosage in transdermal form.

8. The method of claim 7 wherein said transdermal form is selected from the group consisting of transdermal gels, transdermal solutions, transdermal or nasal sprays, and transdermal patches.

9. The method of claim 1 wherein said method of treating comprises a subcutaneous implant.

10. The method of claim 1 wherein said method of treating comprises providing said predetermined dosage in the form of a nasal spray.

\* \* \* \* \*